(12) United States Patent
Jain et al.

(10) Patent No.: US 10,422,013 B2
(45) Date of Patent: Sep. 24, 2019

(54) QUANTITATIVE MEASUREMENT OF HEPATITIS B VIRUS CCCDNA

(71) Applicant: JBS Science Inc., Doylestown, PA (US)

(72) Inventors: Surbhi Jain, Doylestown, PA (US); Jamin Dean Steffen, Yardley, PA (US); Wei Song, Audubon, PA (US)

(73) Assignee: JBS Science Inc., Doylestown, PA (US)

( * ) Notice: Subject to any disclaimer, the term of this patent is extended or adjusted under 35 U.S.C. 154(b) by 167 days.

(21) Appl. No.: 15/433,839

(22) Filed: Feb. 15, 2017

(65) Prior Publication Data

US 2017/0233832 A1 Aug. 17, 2017

Related U.S. Application Data

(60) Provisional application No. 62/295,481, filed on Feb. 15, 2016.

(51) Int. Cl.
*C12Q 1/68* (2018.01)
*C12Q 1/70* (2006.01)
*C12Q 1/686* (2018.01)

(52) U.S. Cl.
CPC ............. *C12Q 1/706* (2013.01); *C12Q 1/686* (2013.01)

(58) Field of Classification Search
CPC ... C12Q 1/686; C12Q 1/706; C12Q 2523/125
See application file for complete search history.

(56) References Cited

U.S. PATENT DOCUMENTS

2004/0058314 A1 3/2004 He et al.

OTHER PUBLICATIONS

Chowdhury et al., "Concerted Action of Activation-Induced Cytidine Deaminase and Uracil-DNA glycosylase Reduces Covalently Closed Curcular DNA of Duck Hepatitis B Virus", FEBS Letters 587, 2013, pp. 3148-3152.
International Search Report and Written Opinion for corresponding International Application No. PCT/US/201/017999, dated Jun. 9, 2017.

*Primary Examiner* — David C Thomas
(74) *Attorney, Agent, or Firm* — PATTAO, LLC; Junjie Feng

(57) ABSTRACT

Hepatitis B Virus (HBV) infection results in the entry of viral genomic DNA into host liver cells. This viral relaxed circular DNA (rcDNA) is transported into the nucleus and converted into covalent closed-circular DNA (cccDNA), which serves as a template for viral transcription. Elimination of cccDNA is needed to cure HBV infection, which remains a major therapeutic challenge. A robust and sensitive method to measure cccDNA described here is useful to facilitate drug development and to monitor efficacy of therapy. A set of primers were designed in combination with sodium bisulfite treatment of viral DNA, allowing specific amplification of cccDNA without interfering amplification of rcDNA. This method can be used to further guide therapeutic development, and to provide a non-invasive alternative to monitoring of HBV-infected patients undergoing antiviral treatments.

18 Claims, 16 Drawing Sheets

Specification includes a Sequence Listing.

BS-ccDNA assay design using BS-converted PLUS strand sequence

TaqMan Probe

BS-Plus Fwd
5'- TTTGTGAATGTGTATTTGTTTATTTATGTATGAATGAACAATTATGTGAAGTT -3'  PLUS
3'- AACACTTACACATAATAACAAATAAAACATTCATACTTACTTGTTAATACACTTCAA -5'  reverse complement of PLUS
BS-Plus Rev

```
genotypeF  tgaacgccccctcgaagcttgccaacagtcttacataagcggactcttggactttcaggaa  1680
genotypeH  tgacgcccctttggaacttgccaacaacttacataagaggactcttggactttcgcccc  1680
genotypeA  tgaacgccatcaggtcctgcccaaggtcttatataagaggactcttggactcccagcaa  1680
genotypeB  tgaacgccaccaggtctttgccaagtcttacataagaggactcttggactctcagcaa  1680
genotypeC  tgaacgccaccaggtctttgccaagtcttacataagaggactcttggactctcagcaa  1680
genotypeG  tgaacgcctctcatcatctaccaaggcagttatataagaggactcttggactgttgtta  1680
genotypeD  tgaacgccacgaaatcttgcccaagatcttatataagaggactcttggactctccacaa  1680
genotypeE  tgacgccaccagatcttgcccaagtcttacataagaggactcttggactctctgcaa  1680
           *  *****   *      *    *     *   * **** ********* ****
```

FIG. 4B

|  | Patient | Actin copies/ul | | % Recovery |
| --- | --- | --- | --- | --- |
|  |  | Before BS | After BS |  |
| Tissue | 1 | 3.4E+04 | 3.2E+04 | 93.8 |
|  | 2 | 4.6E+04 | 4.2E+04 | 91.8 |
|  | 4 | 3.6E+04 | 2.7E+04 | 75.1 |
|  | 5 | 4.6E+04 | 4.6E+04 | 100.5 |
|  | 6 | 7.0E+04 | 7.2E+04 | 102.9 |
| Serum | 2 | 1.7E+05 | 1.6E+05 | 97.1 |
|  | 3 | 1.4E+05 | 1.3E+05 | 93.4 |
|  | 4 | 9.3E+04 | 7.1E+04 | 76.7 |
|  | 5 | 2.0E+05 | 2.2E+05 | 107.7 |
|  | 6 | 1.1E+05 | 1.3E+05 | 119.5 |

FIG. 8

QUANTITATIVE MEASUREMENT OF HEPATITIS B VIRUS CCCDNA

CROSS-REFERENCE TO RELATED APPLICATION

The present application claims priority to U.S. Provisional Application No. 62/295,481, filed Feb. 15, 2016, the contents of which are hereby incorporated by reference in its entirety.

REFERENCE TO SEQUENCE LISTING SUBMITTED ELECTRONICALLY

The content of the electronically submitted sequence listing, file name cccDNA_SeqListing.txt, size 11,611 bytes; and date of creation Feb. 11, 2017, filed herewith, is incorporated herein by reference in its entirety.

FIELD OF THE INVENTION

The present disclosure relates generally to methods and kits for detection or quantification of closed covalent circular DNA (cccDNA) (e.g., of Hepatitis B virus (HBV)), and more specifically relates to a method for detecting or quantifying cccDNA separately from relaxed circular DNA (rcDNA, or RC-DNA) in a biological sample infected with HBV.

BACKGROUND

HBV infection is a global public health concern. Worldwide, 240 million people are chronically infected with HBV (Lavanchy and Kane 2016). Infection with HBV causes acute and chronic hepatitis leading to liver cirrhosis and hepatocellular carcinoma (Kew M C 2010).

Current therapy for HBV infection is limited, suppressing only viraemia without completely eliminating the virus, mainly due to the persistence of cccDNA (Tang, Yau et al. 2014). Withdrawal of therapy results in a rebound for most of patients, which has suggested the presence of a viral remnant responsible for persistent infection (Abdelhamed, Kelley et al. 2002). In patients undergoing antiviral therapy who discontinue treatment, HBV can reactivate from cccDNA (Petersen J 2007). To monitor the persistence of cccDNA in the liver, repeated liver biopsies are required, which are hazardous, uncomfortable, and costly to the patient (Wu, Johnson et al. 2014, Zhong, Hu et al. 2014, Shi, Sun et al. 2015). As cccDNA can also be found in the blood, especially after liver damage, its detection in serum or plasma allows the efficacy of antiviral therapy and the extent of liver damage to be evaluated without resorting to liver biopsies (Wong, Yuen et al. 2004, Takkenberg, Zaaijer et al. 2009).

After HBV infection, viral DNA is transferred to the nucleus of infected hepatocytes where rcDNA is released into the host cytoplasm. The viral DNA is eventually transported into the nucleoplasm where it is converted to cccDNA. Disguised as a minichromosome, the presence of cccDNA in the host nucleus serves as a template for continued virion transcription of messenger RNA in the hepatocyte nucleoplasm (Levrero, Pollicino et al. 2009, Nassal 2015). Thus, persistence of cccDNA remains an obstacle in clearing HBV by conventional antiviral therapy in chronically infected people, who remain at risk of developing advanced liver disease. Interestingly, there is small percentage of patients who clear HBV S-antigen (HBVsAg) by conventional anti-viral therapy alone, indicating cccDNA can be eliminated (Tavis, J E et al. 2013). This "cured" population can be withdrawn from life-long antiviral therapy, which is costly and has unknown side effects, if their cccDNA levels can be measured. A sensitive and specific method for quantification of cccDNA levels from liver biopsy or body fluids is thus highly desired to identify this "cured" population.

Elimination of cccDNA is the ultimate goal of HBV drug development research in finding a cure for HBV infection. A sensitive and specific method for quantification of cccDNA is highly desirable.

SUMMARY

The present disclosure provides a method and a kit for detecting or quantifying a closed covalent circular DNA (cccDNA) in a DNA sample containing the cccDNA and a non-cccDNA.

In a first aspect, a method is disclosed. The method can comprise the following steps:
  i) treating the DNA sample to abolish a complementary feature of, and to thereby prevent reannealing of two strands of, a double stranded DNA molecule in a treated DNA sample; and
  ii) performing an amplification assay on the treated DNA sample such that the cccDNA, but not the non-cccDNA, can give rise to an amplified product.

Herein in the DNA sample, the non-cccDNA is of a substantially same DNA sequence as the cccDNA, but has a different form (e.g. a relaxed circular form, or rcDNA) from the cccDNA.

The DNA sequence can be from HBV, and the HBV DNAs in the DNA sample can thus include a cccDNA form and a non-cccDNA form (e.g. rc DNA or other intermediate forms) of the HBV genome DNA. The DNA sequence can also be obtained from other species, or can be an artificial sequence.

Herein the DNA sample can be obtained from a biological sample such as a tissue or a body fluid, and the body fluid can be serum, plasma, blood, urine, or saliva. The method and the kit can be used in a research setting or in a clinical setting.

The method and the kit can be used to characterize, such as to detect or to quantify, the cccDNA in a DNA sample. In one application in the field of HBV diagnosis, management, and prognosis, the method and the kit can be used to assess the severity of liver damage in patients infected with HBV, or can be used to monitor the efficiency of anti-viral therapy in patients infected with HBV.

According to some embodiments of the present disclosure, the method can further comprise, prior to step i), a step of obtaining the DNA sample from a biological sample.

Herein the DNA sample can be obtained, isolated, or extracted from a biological sample, which can be carried out by any standard method including, but not limited to, ethanol precipitation, phenol-chloroform extraction, minicolumn purification, or any relevant commercially available kit (e.g., Thermo Fisher PureLink® Genomic DNA kit).

According to some embodiments of the method, in step i) the DNA sample can be treated by a chemical reagent, which is configured to alter sequences of, and to thereby abolish the complementary feature of, the two strands of the double stranded DNA molecule in the treated DNA sample.

The chemical reagent as described above can act by causing a deamination reaction, and can be selective for a particular nucleotide (e.g. cytosine) or non-selective (e.g.

adenosine and cytosine). The chemical reagent can be nitrous acid, sodium nitrite, nitrosamines, or sodium bisulfite. The chemical reagent can act by causing other reactions on the strands of the DNA molecules.

According to some embodiments of the method, the amplification assay in step ii) is performed with a pair of primers, configured to respectively anneal to two strategic locations on the DNA sequence, and together configured to be able to generate an amplified product from the cccDNA, but not from the non-cccDNA.

In some embodiments, the amplification assay in step ii) can comprise a real-time polymerase chain reaction (PCR), configured to quantify the cccDNA based on the amplified product.

The two strategic locations can be respectively on two sides of a known discontinuous region of a discontiguous strand in the non-cccDNA. As such, the pair of primers can be configured to respectively anneal to the two strategic locations of, and to thereby generate an amplified product from a contiguous strand in the treated DNA sample.

In some of the embodiments where the DNA sequence is an HBV DNA, the two strategic locations can be on the two sides of the discontinuous region of the HBV (−) strand in rcDNA, or on the two sides of any one of the gap regions of the HBV (+) strand in rcDNA. According to some embodiments of the method targeting HBV DNA, a forward primer of the pair of primers can comprise a sequence as set forth in any one of SEQ ID NOS: 1-21 (see Table 1), and a reverse primer of the pair of primers can comprise a sequence as set forth in any one of SEQ ID NOS: 22-28 (see Table 1).

According to some other embodiments of the method, the amplification assay in step ii) can be performed further with a probe, configured to anneal to the contiguous strand, but not to the discontiguous strand, in the treated DNA sample, and configured to allow a quantification of the cccDNA. The probe can be labelled with a fluorescent dye and fluorescent quencher at a 5'-end and a 3'-end respectively, configured to allow a quantification of the cccDNA by measuring a fluorescent intensity.

In some of the embodiments where the DNA sequence is an HBV DNA, the probe can comprise a sequence as set forth in any one of SEQ ID NOS: 29-31 (see Table 1).

TABLE 1

Primers used for bisulfite treated DNA (lower-cased nucleotides refer to artificial tag sequences)

Forward primers

| | | |
|---|---|---|
| SEQ ID NO: 1 | 1566-1583 | 5' TTTGTYGGATYGTGTGTA 3' |
| SEQ ID NO: 2 | 1566-1584 | 5' TTTGTYGGATYGTGTGTAT 3' |
| SEQ ID NO: 3 | 1566-1585 | 5' TTTGTYGGATYGTGTGTATT 3' |
| SEQ ID NO: 4 | 1566-1586 | 5' TTTGTYGGATYGTGTGTATTT 3' |
| SEQ ID NO: 5 | 1536-1553 | 5' TTAYGYGGTTTTTTYGTT 3' |
| SEQ ID NO: 6 | 1536-1554 | 5' TTAYGYGGTTTTTTYGTTT 3' |
| SEQ ID NO: 7 | 1536-1555 | 5' TTAYGYGGTTTTTTYGTTTG 3' |
| SEQ ID NO: 8 | 1536-1556 | 5' TTAYGYGGTTTTTTYGTTTGT 3' |
| SEQ ID NO: 9 | 1506-1523 | 5' GTTTYGGTYGATTAYGGG 3' |
| SEQ ID NO: 10 | 1516-1533 | 5' ATTAYGGGGYGTATTTTT 3' |
| SEQ ID NO: 11 | 1566-1586 | 5' gtctcgtgggctcggagatgtgtataagagacagTTTGTYGGATYGTGTGTATTT 3' |
| SEQ ID NO: 12 | 1566-1586 | 5' gctcttcgtggtgtggtgTTTGTYGGATYGTGTGTATTT 3' |
| SEQ ID NO: 13 | 1536-1555 | 5' gctcttcgtggtgtggtgTTAYGYGGTTTTTTYGTTTG 3' |
| SEQ ID NO: 14 | 1536-1555 | 5' TTAYGYGGTTTTTTYGTTTGTGTTT 3' |
| SEQ ID NO: 15 | 1536-1555 | 5' TTAYGYGGTTTTTTYGTTTGTGTT 3' |
| SEQ ID NO: 16 | 1536-1555 | 5' TTAYGYGGTTTTTTYGTTTGTG 3' |
| SEQ ID NO: 17 | 1536-1555 | 5' TTAYGYGGTTTTTTYGTTTGT3' |
| SEQ ID NO: 18 | 1536-1555 | 5' gctcttcgtggtgtggtgTTAYGYGGTTTTTTYGTTTGTTT 3' |
| SEQ ID NO: 19 | 1536-1555 | 5' gctcttcgtggtgtggtgTTAYGYGGTTTTTTYGTTTGTT 3' |
| SEQ ID NO: 20 | 1536-1555 | 5' gctcttcgtggtgtggtgTTAYGYGGTTTTTTYGTTTGTG 3' |
| SEQ ID NO: 21 | 1536-1555 | 5' gctcttcgtggtgtggtgTTAYGYGGTTTTTTYGTTTGT 3' |

Reverse primers

| | | |
|---|---|---|
| SEQ ID NO: 22 | 1604-1628 | 5' AACRTTCACRATAATCTCCATACTA 3' |
| SEQ ID NO: 23 | 1605-1628 | 5' AACRTTCACRATAATCTCCATACT 3' |
| SEQ ID NO: 24 | 1606-1628 | 5' AACRTTCACRATAATCTCCATAC 3' |
| SEQ ID NO: 25 | 1607-1628 | 5' AACRTTCACRATAATCTCCATA 3' |
| SEQ ID NO: 26 | 1608-1628 | 5' AACRTTCACRATAATCTCCAT 3' |
| SEQ ID NO: 27 | 1609-1628 | 5' AACRTTCACRATAATCTCCA 3' |
| SEQ ID NO: 28 | 1606-1628 | 5' gctcttcgtggtgtggtgAACRTTCACRATAATCTCCATAC 3' |

Fluorescent primers

| | | |
|---|---|---|
| SEQ ID NO: 29 | 1568-1602 | 5' 6FAM-TTGTYGGATYGTGTGTATTTYGTTTTATTTTTGTA-BBQ 3' |
| SEQ ID NO: 30 | 1589-1605 | 5' 6FAM-TTTTAT + T + T + T + T + G + TAY + G + TA + BBQ 3' ("+" indicates LNA) |
| SEQ ID NO: 31 | 1566-1581 | 5' 6FAM-TTTgTY + g + gATY + gT + gT + g-BBQ 3' ("+" indicates LNA) |

In a second aspect, a kit for detecting or quantifying a cccDNA in a DNA sample containing the cccDNA and a non-cccDNA of a substantially same DNA sequence as, and of a different form from, the cccDNA, is disclosed.

The kit comprises a chemical reagent and a pair of primers. The chemical reagent is configured to abolish a complementary feature of, and to thereby prevent reannealing of two strands of, a double stranded DNA molecule in the DNA sample treated therewith. The pair of primers comprise a forward primer and a reverse primer, and are configured to respectively anneal to two strategic locations on the DNA sequence, and together are configured to be able to generate an amplified product from the cccDNA, but not from the non-cccDNA.

In some embodiments of the kit, the chemical reagent comprises at least one of the following four reagents: nitrous acid, sodium nitrite, nitrosamines, and sodium bisulfite.

In the kit, the two strategic locations can be respectively on two sides of a known discontinuous region of a discontiguous strand in the non-cccDNA, and the pair of primers can be configured to respectively anneal to the two strategic locations of, and to thereby generate an amplified product from a contiguous strand in the treated DNA sample.

According to some embodiments of the present disclosure, the kit can further comprise a probe, which is configured to anneal to the contiguous strand, but not to the discontiguous strand, in the treated DNA sample and configured to allow a quantification of the cccDNA.

The probe can be labelled with a fluorescent dye and fluorescent quencher at a 5'-end and a 3'-end respectively. The fluorescent dye can comprise at least one of 6-carboxy-fluorescein, hexachloro-6-carboxyfluorescein, tetrachloro-6-carboxyfluorescein, FAM (5-carboxy fluorescein), HEX (2', 4',5',7'-tetrachloro-6-carboxy-4,7-dichlorofluorescein), or Cy5 (cyanine-5). The fluorescent quencher can comprise at least one of 6-carboxytetramethyl-rhodamine, TAMRA (5-Carboxytetramethylrhodamine), BBQ (BlackBerry Quencher), or BHQ3 (black hole quencher 3).

The kit can further comprise a DNA polymerase, polymerase buffer, dNTPs, or a combination thereof.

According to some embodiments of the present disclosure, the kit can be customized for HBV. Specifically, the cccDNA comprises a ccDNA form of Hepatitis B virus (HBV), and the non-cccDNA comprises a relaxed circular DNA (rcDNA) form of Hepatitis B virus (HBV).

As such, the forward primer can comprise a sequence as set forth in any one of SEQ ID NOS: 1-21 (see Table 1), and the reverse primer can comprise a sequence as set forth in any one of SEQ ID NOS: 22-28 (see Table 1).

In some preferred embodiments, the reverse primer comprises a sequence as set forth in SEQ ID NO: 24, and the forward primer comprises a sequence as set forth in SEQ ID NO: 11, SEQ ID NO: 12, or SEQ ID NO: 17.

Some embodiments of the kit for HBV can also comprise a probe, which comprises a sequence as set forth in any one of SEQ ID NOS: 29-31.

In another aspect, the present disclosure provides a method of detecting in a sample cccDNA distinguishably from rcDNA. The method comprises: (a) treating the sample with a nucleotide converter reagent; and (b) detecting the cccDNA by a PCR procedure.

In some embodiments of the method, the nucleotide converter reagent converts C residues to U residues. As such, the nucleotide converter reagent can be a deaminator (i.e. a chemical reagent causing a deamination reaction to the nucleotides). The above nucleotide converter reagent can be selected from the group consisting of nitrous acid, sodium nitrite, nitrosamines, sodium bisulfite, and combinations thereof.

According to some embodiments of the present disclosure, the PCR procedure uses primers that span a discontinuous region. The pair of primers can be configured to respectively anneal to two strategic locations on two sides of the discontinuous region, and together configured to be able to generate an amplified product from the cccDNA, but not from the non-cccDNA.

According to some embodiments of the present disclosure, the PCR procedure further uses a probe, wherein the probe is configured to anneal to a contiguous strand, but not to a discontiguous strand.

BRIEF DESCRIPTION OF THE DRAWINGS

FIGS. 2A-2G depict a cccDNA PCR assay, designated as "BS-cccDNA PCR assay", as compared to currently available cccDNA PCR assays from literature.

FIGS. 4A and 4B show a multi-sequence analysis of the 8 genotypes of the HBV virus (A-H) in the DR2 region that is targeted for PCR.

FIG. 8 shows that bisulfite treatment (BS) does not significantly reduce the copy detection of a DNA target region.

DETAILED DESCRIPTION

Figure 1:
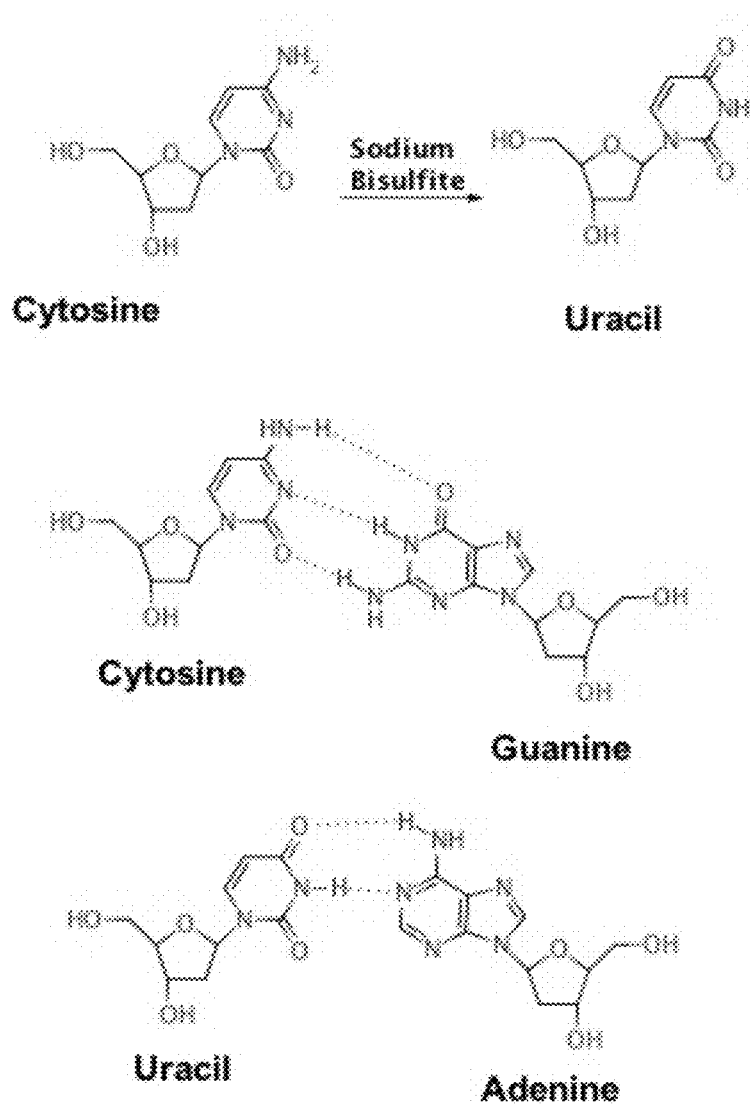
FIG. 1 depicts the molecular conversion of a cytosine nucleotide to a uracil nucleotide through deamination by Sodium Bisulfite. As shown, the complement base pairing nucleotide with cytosine is guanine, and with uracil is adenine.

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

Various embodiments will be described in detail through the displayed figures. Reference to these embodiments do not limit the scope of the claims. Provided examples are not meant to limit the scope of methods and claims herein, but rather describe example uses of the embodiments of the claims.

As used in this specification and the appended claims, the singular forms "a", "an", and "the" include plural referents unless the content clearly dictates otherwise. Thus, for example, reference to "a cell" includes a combination of two or more cells, and the like.

The term "nucleotide sequence" and "oligonucleotide" as used herein indicate a polymer of repeating nucleic acids (Adenine, Guanine, Thymine, Cytosine, and Uracil) that is capable of base-pairing with complement sequences through Watson-Crick interactions. This polymer may be produced synthetically or originate from a biological source.

The term "deoxyribonucleic acid" and "DNA" refer to a polymer of repeating deoxyribonucleic acids.

The term "ribonucleic acid" and "RNA" refer to a polymer of repeating ribonucleic acids.

The term "disease" or "disorder" is used interchangeably herein, and refers to any alteration in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailing, ailment, malady, disorder, sickness, illness, complaint, inderdisposion or affectation.

"Gene" is well known in the art, and herein includes non-coding regions such as a promoter or other regulatory sequences or proximal non-coding regions.

A biological sample can comprise of whole tissue, such as a biopsy sample. Other examples of a biological sample comprise biological fluids including, but not limited to, saliva, nasopharyngeal, blood, plasma, serum, gastrointestinal fluid, bile, cerebrospinal fluid, pericardial, vaginal fluid, seminal fluid, prostatic fluid, peritoneal fluid, pleural fluid, urine, synovial fluid, interstitial fluid, intracellular fluid or cytoplasm and lymph, bronchial secretions, mucus, or vitreous or aqueous humor. Biological samples can also include cultured medium. In certain embodiments, the preferred biological fluid is urine.

The term "primer" defines an oligonucleotide sequence that is capable of annealing to a complementary target sequence, thereby forming a partially double-stranded region as a starting point from which a polymerase enzyme can continue DNA elongation to create a complementary strand.

The term "diagnosing" means any method, determination, or indication that an abnormal or disease condition or phenotype is present. Diagnosing includes detecting the presence or absence of an abnormal or disease condition, and can be qualitative or quantitative.

The term "genome" and "genomic" refer to any nucleic acid sequences (coding and non-coding) originating from any living or non-living organism or single-cell. These terms also apply to any naturally occurring variations that may arise through mutation or recombination through means of biological or artificial influence. An example is the human genome, which is composed of approximately $3 \times 10^9$ base pairs of DNA packaged into chromosomes, of which there are 22 pairs of autosomes and 1 allosome pair.

Amplification of a selected, or target, nucleic acid sequence may be carried out by a number of suitable methods. See generally Kwoh et al., 1990, Am. Blotechnol. Lab. 8:14-25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Qβ replicase system and NASBA (Kwoh et al., 1989, Proc. Natl. Acad. Sci. USA 86, 1173-1177; Lizardi et al., 1988, BioTechnology 6:1197-1202; Malek et; and Sambrook et al., 1989, supra). Preferably, amplifications will be carried out using PCR.

Polymerase chain reaction (PCR) is carried out in accordance with known techniques (see, e.g., U.S. Pat. Nos. 4,683,195; 4,683,202; 4,800,159; and 4,965,188, whose disclosures are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophoresis, or using a detectable label in accordance with known techniques, and the like. For a review on PCR techniques, see PCR Protocols, A Guide to Methods and Amplifications, Michael et al. Eds, Acad. Press, 1990.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications.

The term "rcDNA", "RC-DNA" or "relaxed-circular DNA" relates to a form of DNA, which is partially double-stranded, circular but not covalently closed. The (+) strand forms partial double-stranded DNA with the (−) strand, leaving a gap at the 3' end that can vary in length among molecules (Guo, Jiang et al. 2007). For example, HBV genome can exist in the form of rcDNA. In the case of HBV genome, the 5' end of the (−) strand of the rcDNA can be covalently linked to the viral P protein.

The term "cccDNA" or "covalently closed circular DNA" relates to a form of DNA, which is a non-integrated plasmid-like molecule. It differs from rcDNA by not having the (−) strand discontinuity, and not having the (+) strand gap. For example, HBV genome can exist in the form of cccDNA. In the case of HBV genome, cccDNA can be the template for viral RNAs and is responsible for the generation of progeny virions (Guo, Jiang et al. 2007, Nassal 2015).

The technical approach as detailed in the present disclosure has the advantage that the procedures as provided herein are capable of detecting and quantifying solely cccDNA in a patient sample, by removing complementation of HBV (−) strand and (+) strand, and amplifying continuous HBV DNA sequence that is provided by cccDNA, but not by rcDNA.

Disclosed herein are methods for the detection and quantification of cccDNA in a sample of any origin. In some embodiments the sample can be a clinical sample obtained from a patient such as, but not limited to, tissue, blood, serum, plasma, or any other body fluid that can be obtained. In other embodiments, the sample can be a research-based sample such as, but not limited to, cell culture and animal studies.

The present disclosure provides a method enabling highly specific and sensitive quantification and detection of the cccDNA template. By using the method disclosed herein, sodium bisulfate treatment of the DNA is performed, thereby converting the complementary (+) and (−) strands of the HBV genome to non-complementary strands. FIG. 1 depicts the molecular conversion of a cytosine nucleotide to a uracil nucleotide through deamination by Sodium Bisulfite. As shown in FIG. 1, the complement base pairing nucleotide with cytosine is guanine, and with uracil is adenine.

Such separation of the two strands of HBV DNA enables the design of strand specific PCR where the primers are chosen to span the region containing the gap in the (+)-strand and the discontinuity of the (−) strand of the rcDNA, while the region is continuous in cccDNA. Primers are designed to not overlap with human genomic DNA. However, unlike previous approaches, the (+) and (−) strands being treated and kept non-complementary to each other overcomes the challenge of linear extension of the individual primers generating shorter but overlapping products that can anneal to each other and subsequently form an identical amplicon as that from cccDNA. This strategy is truly a cccDNA-specific PCR that can provide discrimination between cccDNA and other forms of this viral genomic DNA such as rcDNA.

FIGS. 2A-2G depict the working principle of the aforementioned cccDNA PCR assay, designated as "BS-cccDNA PCR assay", as compared to currently available cccDNA PCR assays from literature.

Figure 2A:
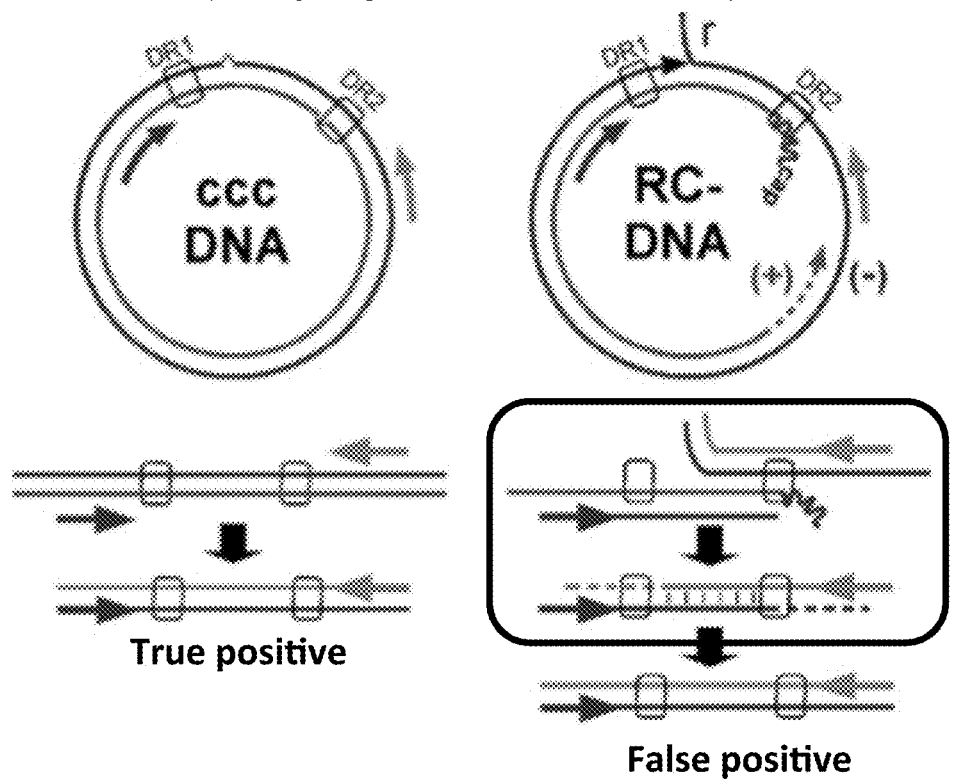

As shown in FIG. 2A, the "false positive" of cccDNA measurement derived from the rcDNA template by current cccDNA PCR assays, as adapted from Nassal, M. 2015 (Nassal 2015). Most current cccDNA PCR assays (or non-BS cccDNA PCR assays) have designed primers on either side of the DR1 and DR2 region, as indicated by arrows. As shown in the boxed diagram, the false positive generated from the rcDNA is mainly due to the linear extension of individual primers that generate shorter, but overlapping products that can anneal to each other and subsequently amplify to form an identical amplicon as that from cccDNA.

Figure 2B:
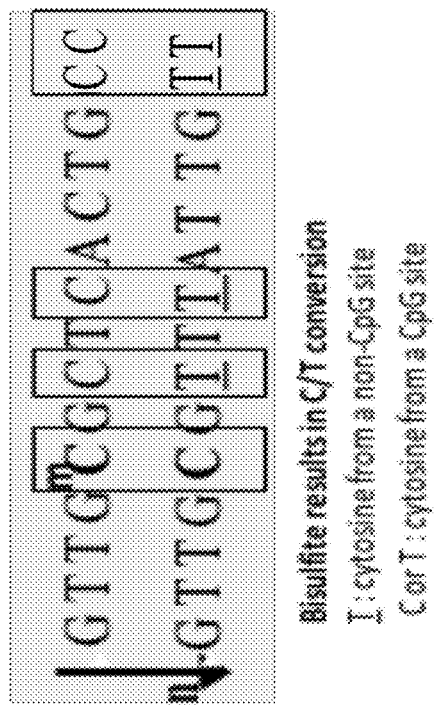
Figure 2B:
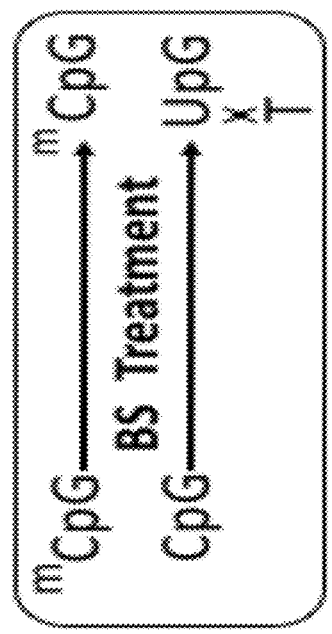

FIG. 2B is an illustration of bisulfite treatment (BS) that results in C/T conversion. One example, shown in the right panel, indicates that after bisulfite treatment, the cytosine "C" at the CpG site remains C if methylated. All unmethylated C's, regardless of their position in the DNA sequence, will be converted to U, which is, similarly to T, complementary to A. Thus the result is an alteration of DNA sequences that abolishes the complementation feature of the Plus (+) and Minus (−) strands of DNA.

Figure 2C:
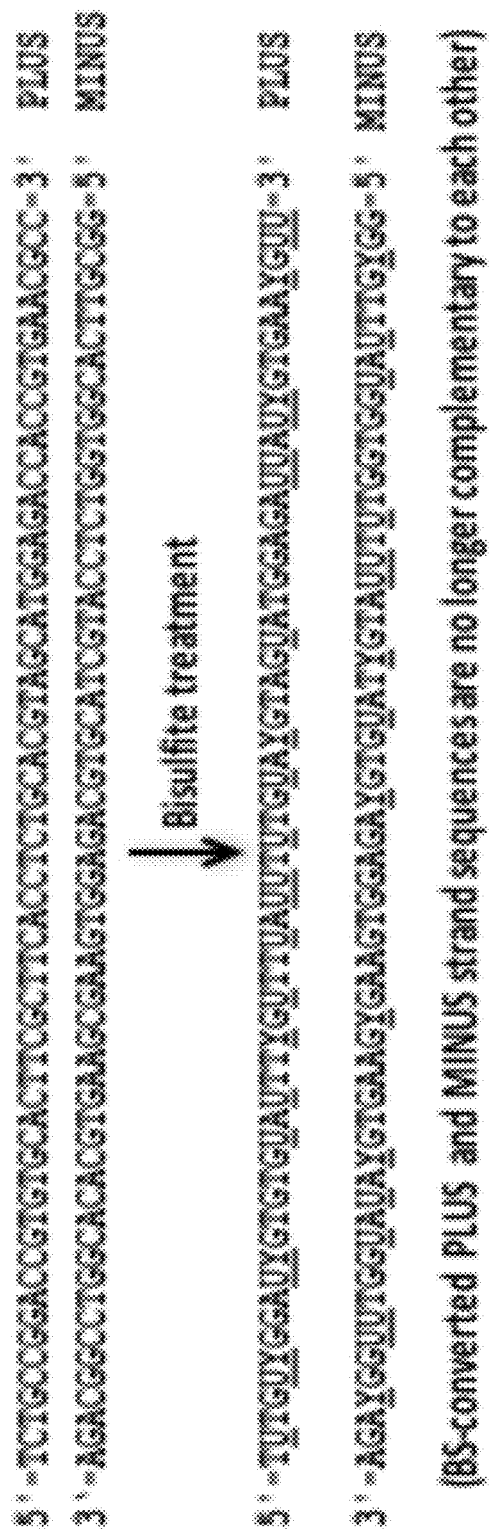

FIG. 2C shows HBV DNA sequences from nt. position 1556-1628 (GenBank accession # NC_003977), used for BS-cccDNA PCR assay design and the altered DNA sequences after bisulfite treatment showing that the Plus and Minus strands are no longer complementary to each other.

FIG. 2D shows "BS-cccDNA" PCR assay design using BS-converted Plus strand sequences. The locations (shaded) and sequences of forward primer, reverse primer, and TaqMan probe are shown.

Figure 2E:
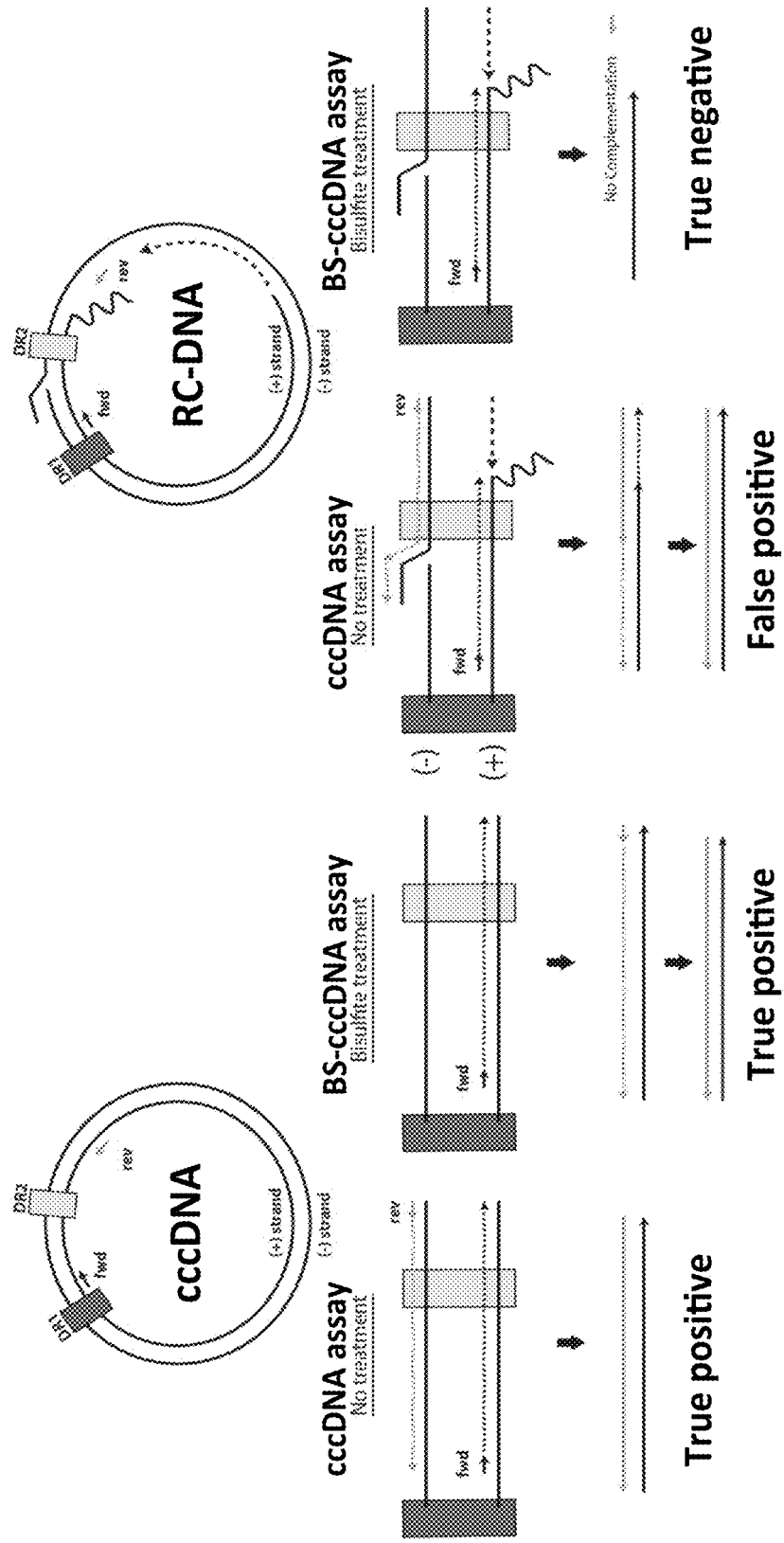

FIG. 2E illustrates schematic comparison of 'BS-cccDNA" and conventional, current, or published "cccDNA" PCR approaches. The diagram illustrates the possible false positive generated if the PCR is performed without abolishing the complementation of the Plus and Minus strands, such as by bisulfite treatment, even if the primer design is at the region that is discontinuous in the Plus strand of rcDNA.

Figure 2F:
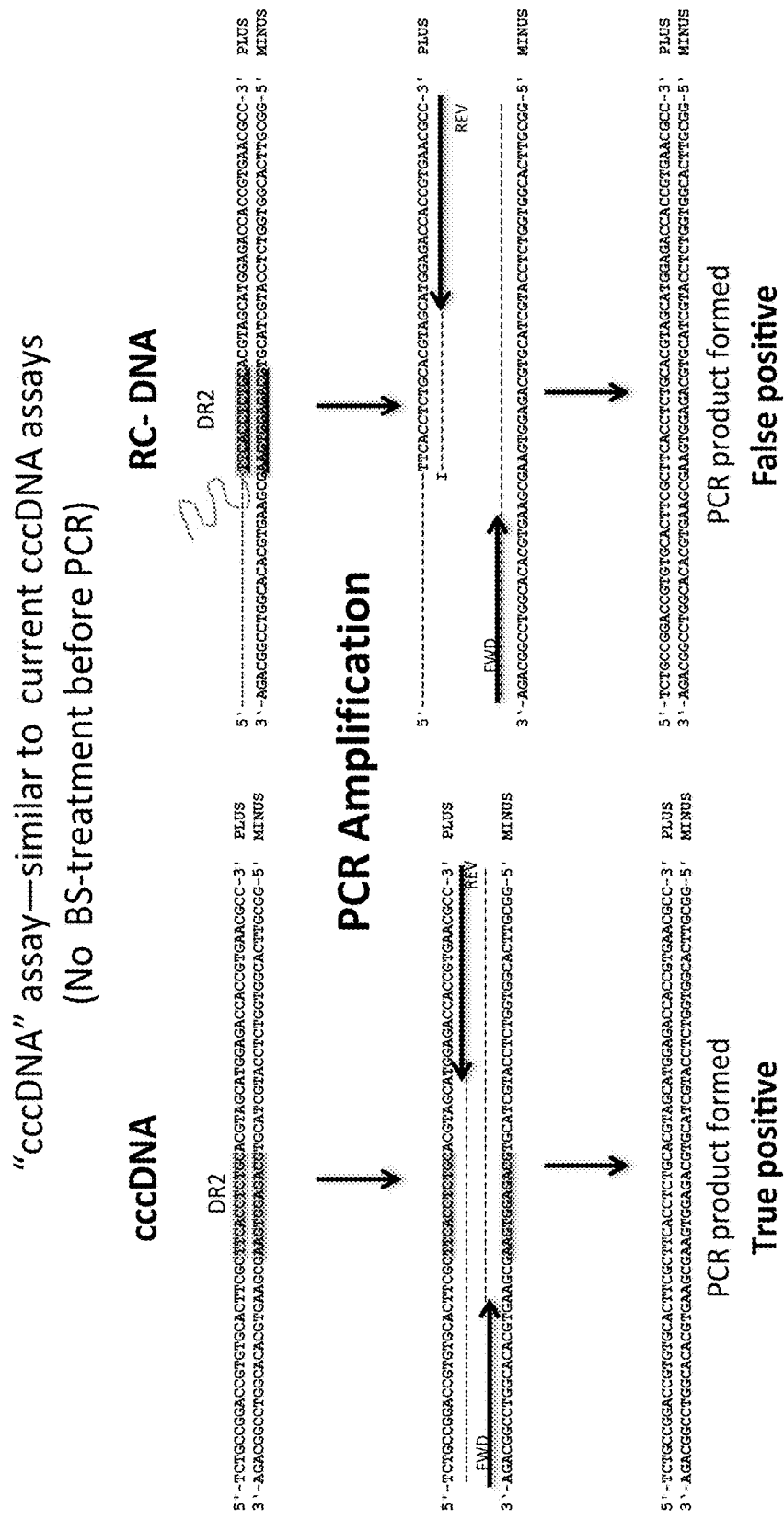

FIG. 2F provides a further detailed illustration by DNA sequences of the false positive generated from the rcDNA template by cccDNA PCR with no bisulfite treatment.

Figure 2G:
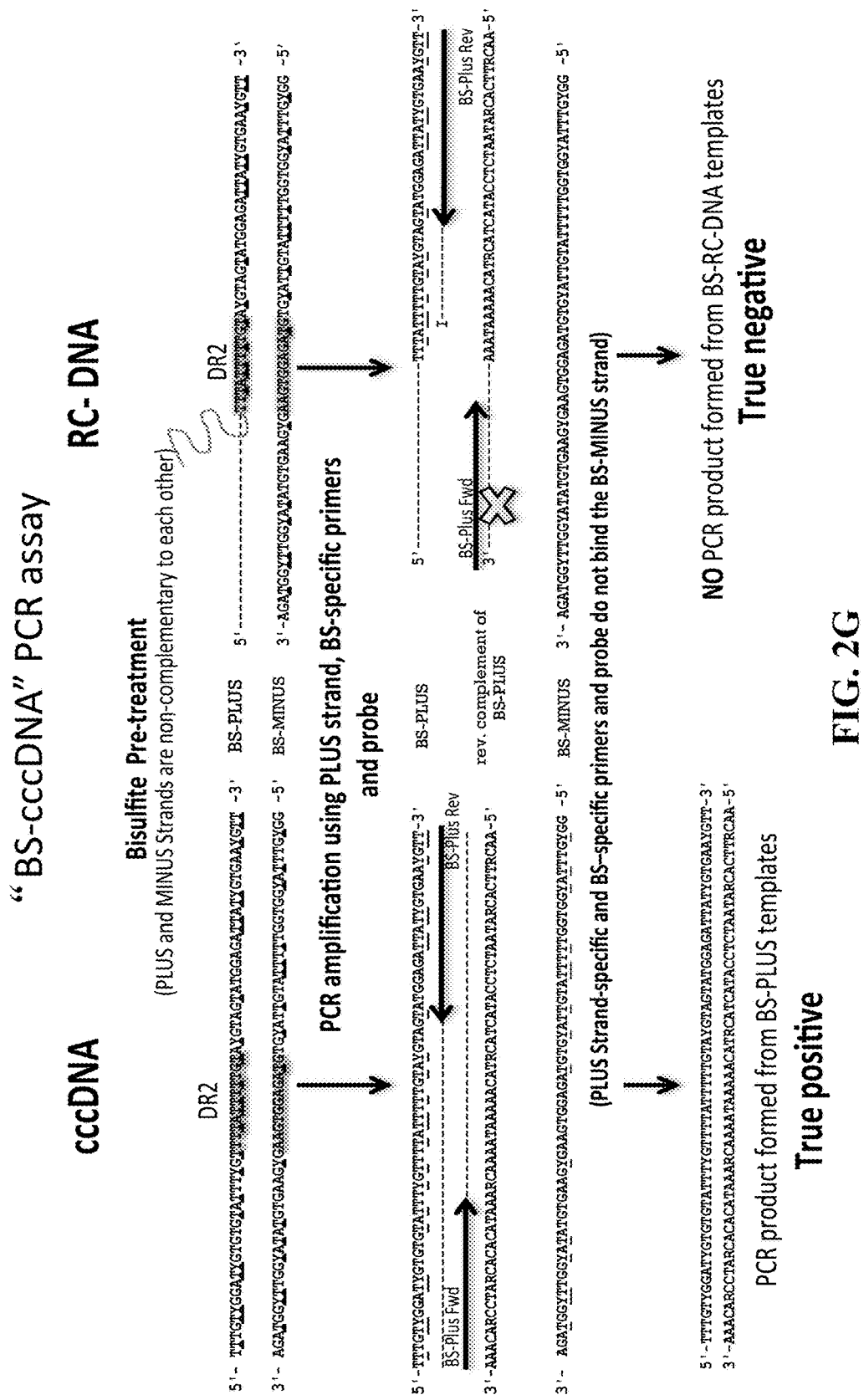

FIG. 2G provides another illustration by DNA sequences of the true positive and true negative generated from cccDNA templates and rcDNA templates, respectively, by "BS-cccDNA" PCR assay including bisulfite treatment of DNA prior to PCR amplification using Plus strand specific and BS-specific primers and probe. Treatment with sodium bisulfite prevents the forward primer from annealing to the (−) strand, and therefore specifically amplifies cccDNA and not rcDNA.

Figure 3:
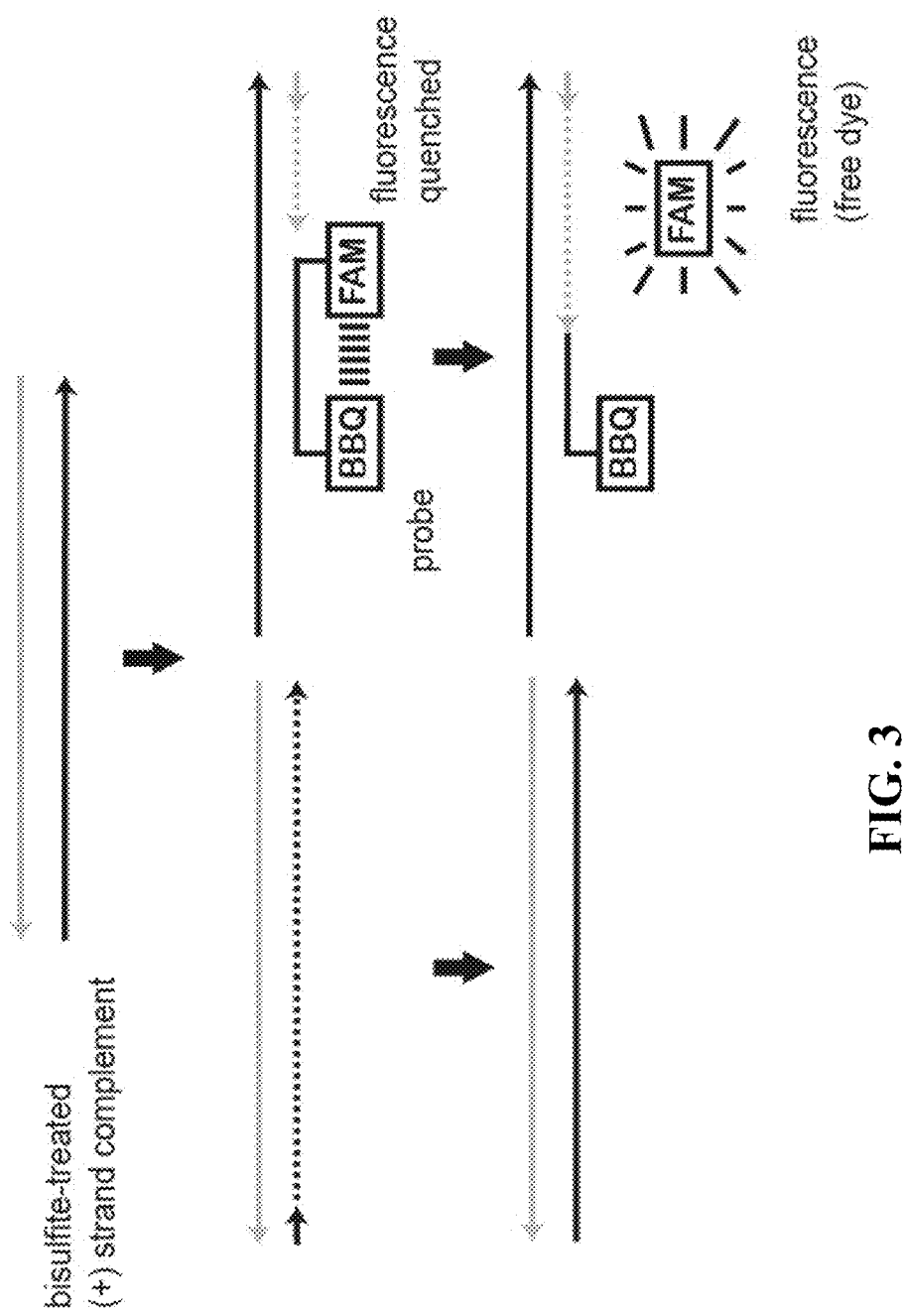
FIG. 3 depicts the detection of HBV cccDNA.

FIG. 3 depicts the detection of HBV cccDNA according to some embodiments of the present disclosure. The complement amplification strand generated from the PCR amplification strategy in FIG. 2E (and FIG. 2G) binds to the probe. When the complementary primer begins to copy this amplification strand, the probe is encountered and digested which releases the dye (FAM) from the quencher (BBQ). This change in fluorescence permits quantitative detection through real-time PCR.

Figure 4A:
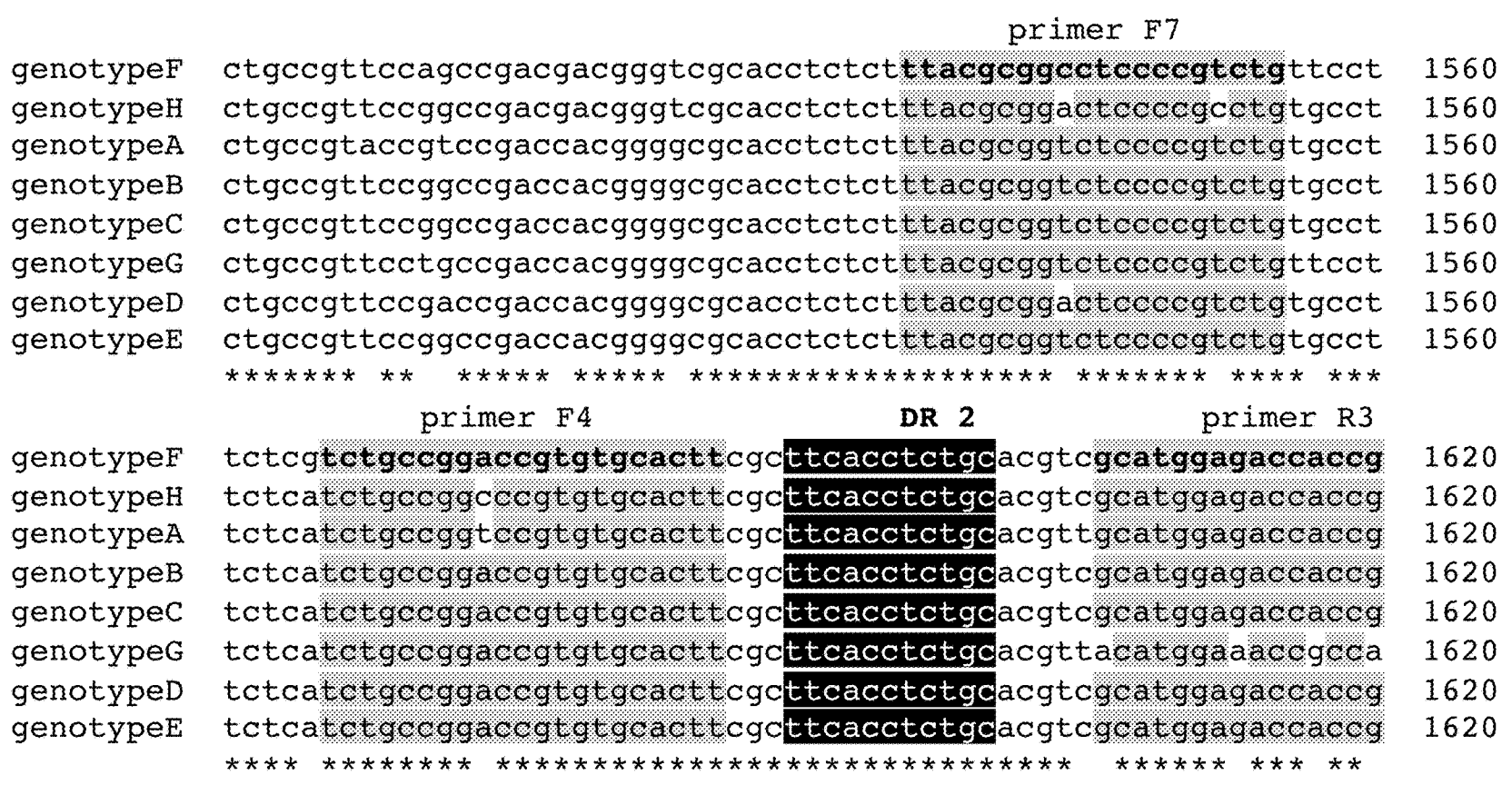

FIGS. 4A and 4B show a multi-sequence analysis of the 8 genotypes of the HBV virus (A-H) in the DR2 region that is targeted for PCR.

Figure 5:
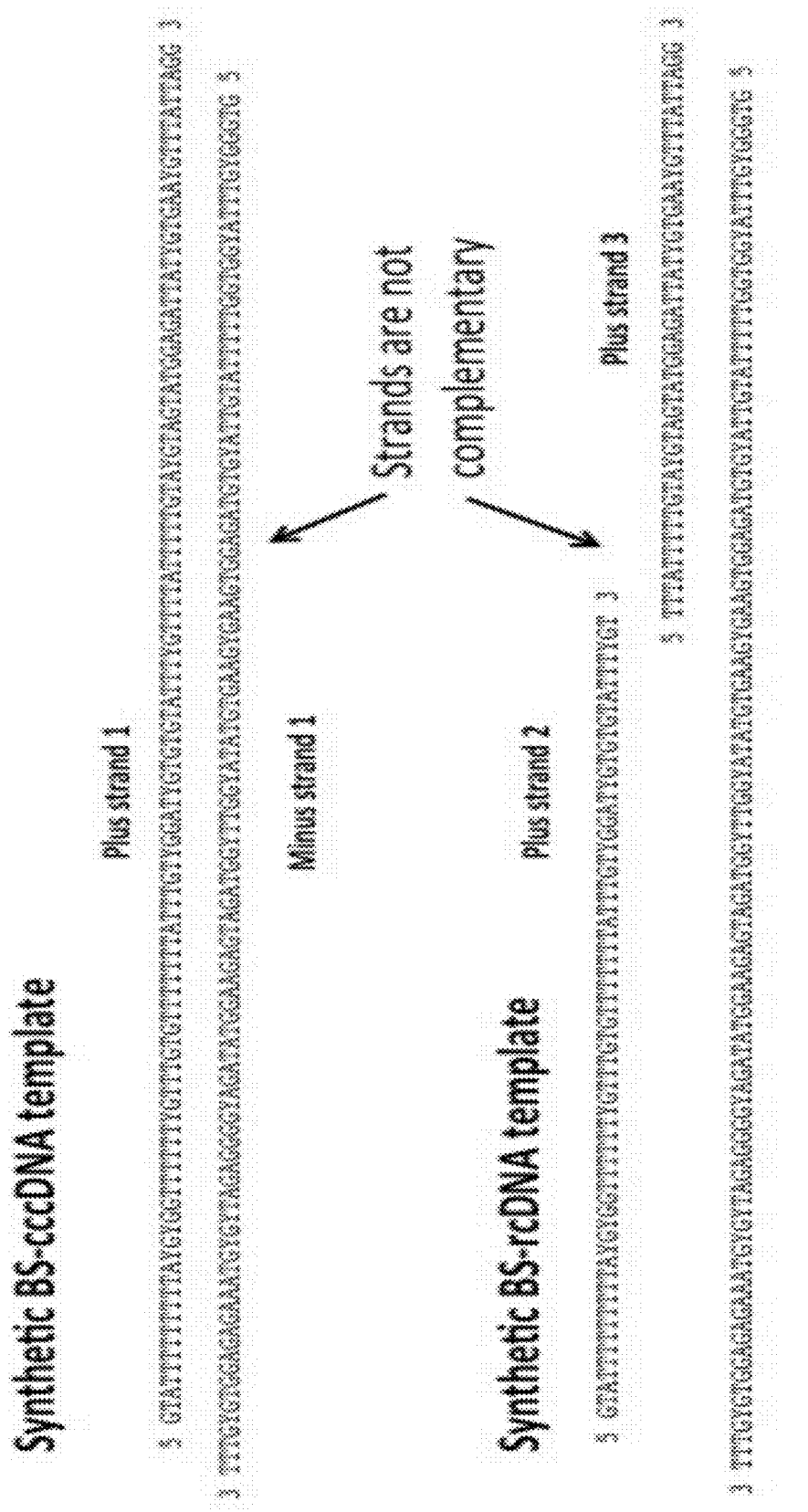
FIG. 5 depicts the two synthetic DNA templates that resemble the bisulfite-converted HBV DNA in the area of interest.

FIG. 5 depicts the two synthetic DNA templates that resemble the bisulfite-converted HBV DNA in the area of interest. Both strands are used, but are not complementary and are single-stranded. The synthetic BS-cccDNA template is composed of two DNA oligos, and the BS-rcDNA is composed of 3 DNA oligos that mimic the discontinuity of the minus strand.

This technology does not depend on the enzymatic Plasmid-safe DNase pretreatment (Singh, Dicaire et al. 2004), although it can be combined if desired. This independence is because the nearly complete (+) strand of rcDNA cannot act as a substrate for this amplification reaction. A TaqMan probe designed for the bisulfite treated region overlapping the (+) strand gap ensures specific quantification of cccDNA. This method also allows for quantification of total HBV DNA as it does not require DNase or exonuclease, thereby preserving integrity of the non-cccDNA background.

The method disclosed herein is suitable for the detection and/or quantification of cccDNA of any origin such as, but not limited to, serum from patients with hepatitis B to evaluate the severity of liver damage and to assess the efficacy of antiviral therapy.

In patients undergoing antiviral therapy who discontinue treatment, HBV can reactivate from cccDNA (Petersen J 2007). To monitor the persistence of cccDNA in the liver, repeated liver biopsies are required, which are hazardous and uncomfortable to the patient, and costly (Wu, Johnson et al. 2014, Zhong, Hu et al. 2014, Shi, Sun et al. 2015). As cccDNA can also be found in the blood, especially after liver damage, its detection in serum or plasma allows the efficacy of antiviral therapy and the extent of liver damage to be evaluated without resorting to liver biopsies (Wong, Yuen et al. 2004, Takkenberg, Zaaijer et al. 2009).

A sensitive and specific method for quantification of cccDNA has been highly desired, although development of such an assay has proved difficult due to factors such as the low copy number of cccDNA per cell (Nassal 2015). Cell lines have been generated to increase cccDNA copy number per cell (Singh, Dicaire et al. 2004), allowing for detection by southern blot (Liu, Campagna et al. 2013). However Southern blot is not an appropriate method for detection of cccDNA from patient samples. PCR based approaches have also been developed by designing primers that target the (−) strand overlap and the (+) strand gap region of HBV DNA (He, Wu et al. 2002). While this approach can be made selective for HBV DNA, it cannot discriminate between cccDNA and rcDNA forms of the HBV genome (Nassal 2015). Other techniques such as rolling circular amplification and Invader technology have been described, although a true and clean quantification is not obtainable (Wong, Yuen et al. 2004, Zhong, Hu et al. 2014, Nassal 2015).

Previous studies have shown that serum HBV cccDNA levels correlate well with intrahepatic cccDNA content in chronically infected HBV patients (Li, Zhao et al. 2014). Detection of serum cccDNA may thus serve as a reliable and sequential monitoring of intrahepatic cccDNA levels without the requirement for repeated liver biopsies. Quantitative detection of cccDNA in serum would allow evaluation of efficacy and guidance of antiviral therapy (Chen, Sze et al. 2004). While methods for detection of HBV cccDNA have been reported, there are currently no commercially available kits for cccDNA detection and quantification.

A feasible detection method for cccDNA will be important for development of new antiviral agents against HBV, monitoring of viral progression and resistance, and discovery of extrahepatic infection. Much of the HBV drug discovery effort is aimed towards development of improved antivirals that cure rather than suppress HBV (Ahmed, Wang et al. 2015, Kumar, Perez-del-Pulgar et al. 2016). This will require very precise and sensitive detection methods of cccDNA as it presents at very low concentrations of 0.1-1 copies on average per cell, per infected liver. In the coming years, a substantial proportion of HBV infected persons who undergo antiviral therapy will also benefit from access to a facile diagnostic method for the detection of cccDNA.

It is to be understood that the above described embodiments are merely illustrative of numerous and varied other embodiments which may constitute applications of the principles of the present disclosure. Such other embodiments may be readily devised by those skilled in the art without departing from the spirit or scope of this disclosure and they shall be deemed within the scope of the present disclosure.

All references cited in this application are incorporated by reference into this application in their entireties.

The technological approach as described in the disclosure is further illustrated by the following non-limiting examples.

Example 1: The Recovery of DNA After Bisulfite Treatment as Detected by PCR

Complementary strands of double-stranded DNA can be made non-complementary by bisulfite treatment, which converts the cytosine nucleotide to uracil, as illustrated in FIG. 2B.

Here, Qiagen Epitect Bisulfite conversion kits (Qiagen, CA) and Zymo Research EZ DNA Methylation Gold kits (Zymo Research, Zymo Research Corporation, CA) were used according to the manufacturer's specifications for bisulfite conversion. DNA from human HCC tissue samples were bisulfite-treated and tested with specific assays before and after bisulfite-treatment. A region on the constitutive gene, actin, was used for comparison by running assays that target the non-bisulfite treated DNA region and the bisulfite-treated DNA region (see FIG. 8).

FIG. 8 shows that bisulfite treatment (BS) does not significantly reduce the copy detection of a DNA target region. Primers that amplify a short product in the actin gene for both non-bisulfite treated and bisulfite treated DNA were compared, and revealed no major difference. 5 tissue samples and 5 serum samples from patients infected with HBV were used for this comparison.

The comparison of the before and after bisulfite treatment on the actin gene reveals that bisulfite treatment recovery is high as per the manufacturers specifications, and reveals the suitability for use in BS-cccDNA assay described herein.

Example 2: DNA Quantification by Real-Time Polymerase Chain Reaction (RT-PCR)

Total HBV DNA was quantified by real-time PCR using the LightCycler PCR instrument (Roche Biochemical, Germany) and the LightCycler Probe Master Mix (Roche Biochemical, Germany) according to the manufacturer's specification. Primers for bisulfite treated total HBV DNA (forward, 5'-TTATGTTAATGTTAATATGGGTTTAAA-3'; reverse, 5'-TTCTCTTCCAAAAATAAAACAA-3'; probe, 5'-6FAM-TTAGATAATTATTG+TGG+T+T+T+TA+TA+T-BBQ3') and serially diluted HBV DNA plasmid as quantification standards were used for quantification.

To quantify the bisulfite converted cccDNA, primers (forward, 5'-GTCTCGTGGGCTCGGAGATGTG-TATAAGAGACAGTTTGTYGGATYGTGTGTATTT-3'; reverse, 5'-AACRTTCACRATAATCTCCATAC-3') within the (+) strand gap region were chosen so to prevent amplification of rcDNA. The TaqMan probe 5' 6FAM-TTTTAT+T+T+T+T+G+TAY+G+TA-BBQ-3' was used to detect the amplification product.

Example 3: A 1-Step BS-cccDNA Assay for Detection of cccDNA by Real-Time-PCR

Figure 7:
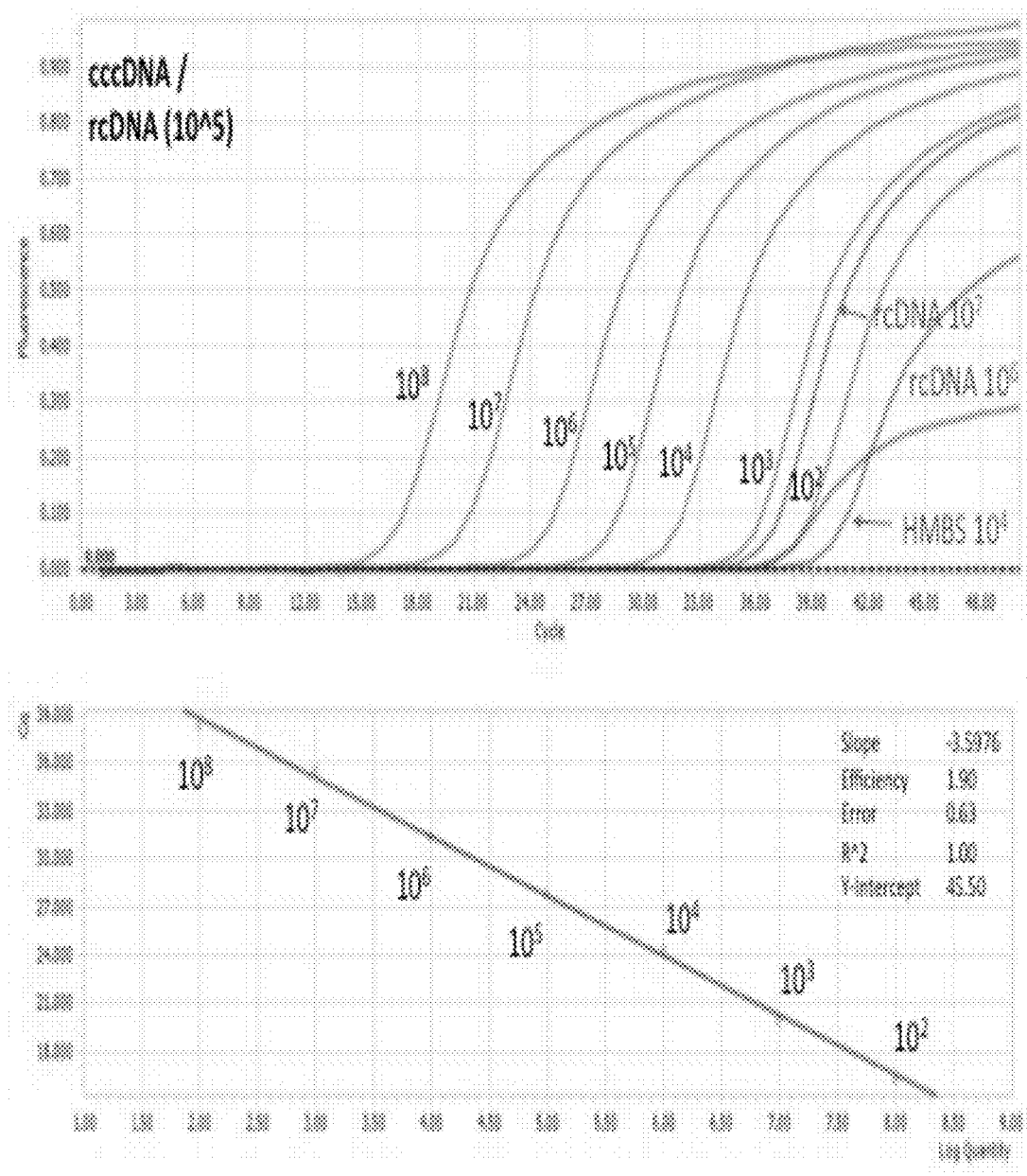
FIG. 7 illustrates the sensitivity of 100 copies of the BS-cccDNA template in the one-step cccDNA assay, and the linearity from $10^8$ to 100 copies of synthetic BS-cccDNA in a background of $10^5$ copies of rcDNA.

FIG. 7 illustrates the sensitivity of 100 copies of the BS-cccDNA template in the one-step cccDNA assay, and the linearity from $10^8$ to 100 copies of synthetic BS-cccDNA in a background of $10^5$ copies of rcDNA. A 10-fold serial dilution of the synthetic HBV templates described in FIG. 5 range from 100 to $10^8$ copies of sensitivity and linearity of the assay. The data are presented as amplification curves (top) and standard curves (bottom).

The one-step real-time PCR was performed using the primer set SEQ ID NO: 11 and SEQ ID NO: 24. Detection of the amplified product was carried out using the SEQ ID NO: 29 as the probe. Human methylated, bisulfite treated DNA was used as a negative control at 10,000 copies, and had no observable amplification. Note, $10^4$ HMBS was amplified at the cp value similar to 10 copies of cccDNA, thus the sensitivity or limit of detection of the 1-step BS-cccDNA is 100 copies in the presence of $10^4$ HMBS background.

The following protocol uses the Roche LightCycler® Real-time PCR instrument using a 10 µl reaction with the Roche DNA Master SYBR® Green I system. The following reagents were added: in order, 5 µl; of the 2×LC probes Master Mix (1× final concentration), 1 µl of PCR grade water, 1 µl of the 10 uM forward primer (SEQ ID NO: 11, 5'-GTCTCGTGGGCTCGGAGATGTGTATAAGAGACA-GTTTGTYGGATYGTGTGTATTT-3'; 1 µM final concentration), 1 µl of 10 µM reverse primer (SEQ ID NO: 24, 5'-AACRTTCACRATAATCTCCATAC-3'; 1 µM final concentration), and 1 µl of 0.2 µM final (SEQ ID NO: 29, 5'-6FAM-TTTTAT+T+T+T+T+G+TAY+G+TA-BBQ-3'; 0.2 µM final concentration). Mix well and add 9 µl of this PCR reaction to 1 µl of the respective DNA template or sample, for a total of 10 µl final volume in a Roche 96-well LightCycler 480 plate. Run the RT-PCR reaction in the following conditions: 95° C. for 5 min., then 95° C. for 10 s, 52° C. for 10 s, 72° C. for 10 s for 45 cycles followed by a cooling program at 40° C. for 30 s.

Example 4: A 2-Step BS-cccDNA Assay for Detection of cccDNA by RT-PCR

Figure 6:
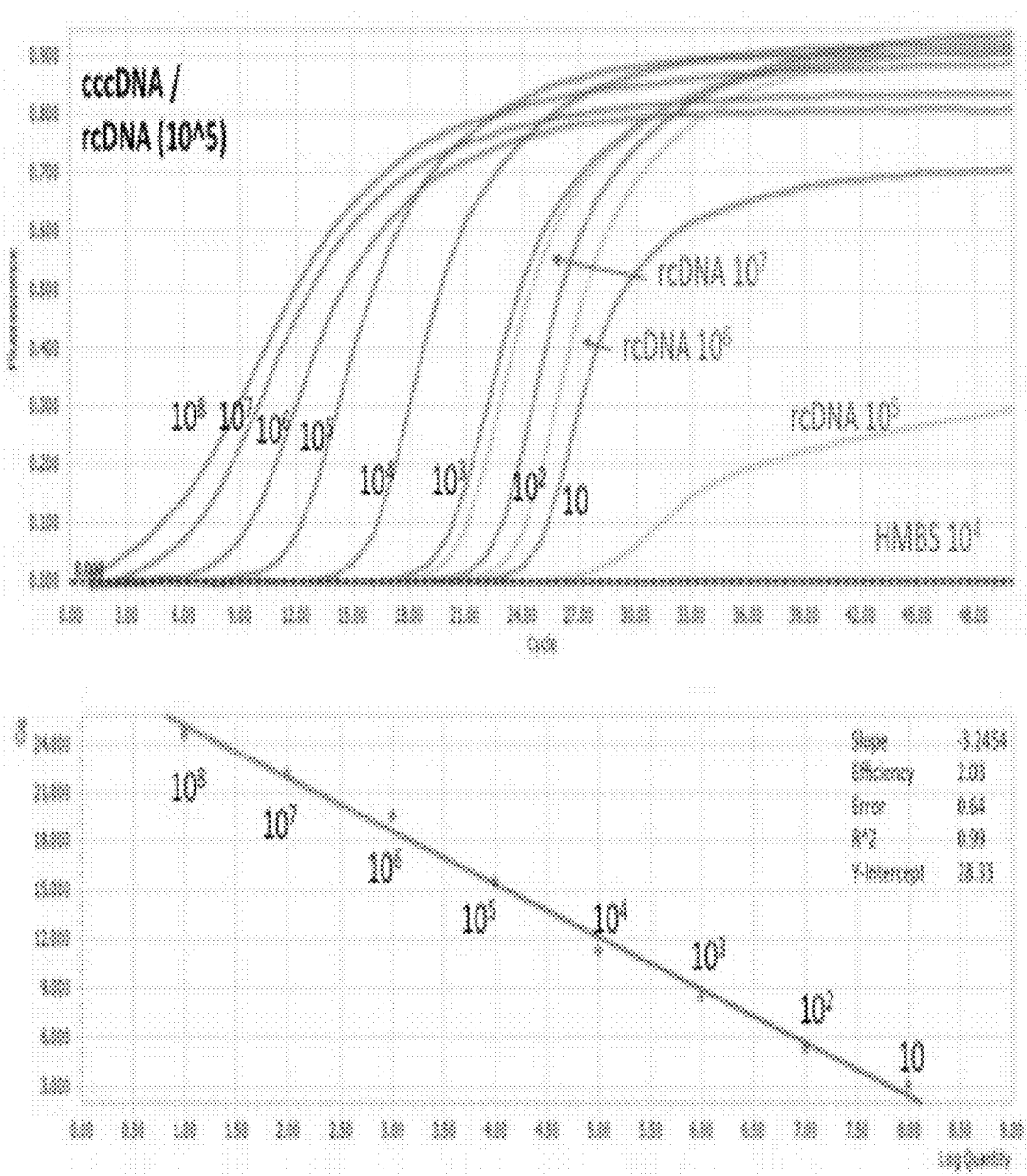
FIG. 6 illustrates the linearity and sensitivity of the two-step BS-cccDNA assay from $10^8$ to 10 copies of the synthetic BS-cccDNA template in a background of $10^5$ copies of BS-rcDNA.

FIG. 6 shows the results from a 2-step BS-cccDNA assay. A 10-fold serial dilution of the synthetic HBV templates described in FIG. 5 range from 10 to $10^8$ copies of sensitivity and linearity of the assay. The data are presented as amplification curves (top) and standard curves (bottom). For the first step, PCR amplification was performed using the primer set SEQ ID NO: 17 and SEQ ID NO: 24. For the second step, PCR was performed using the first step product and the primer set SEQ ID NO: 12 and SEQ ID NO: 24. The amplified product was detected and quantified using the SEQ ID NO: 29 as the probe. Human methylated, bisulfite treated DNA was used as a negative control at 10,000 copies, and had no observable amplification.

Specifically, a PCR reaction was performed as follows: Assembly of a PCR reaction containing 15 ul total volume in a 0.5 mL PCR micro-centrifuge tube. Using the QIAGEN HotStartPlus DNA Taq® Polymerase system (QIAGEN, Valencia, Calif.) add in order 7.9 ul of PCR grade water, 1.5 ul of 10×PCR buffer (1× final concentration), 1.5 ul of 2.5 mM dNTPs (0.25 mM final concentration) 1 µM of the 10 uM forward primer (SEQ ID NO: 17, 5'-TTAYGYGGTT TTTTYGTTTG T-3'; 1 µM final concentration), 1 µl of 10 µM reverse primer (SEQ ID NO: 24, 5'-AACRT-TCACRATAATCTCCATAC-3'; 1 µM concentration), and 0.1 ul Taq Polymerase (final concentration of 0.033 U), and 1 ul of the respective DNA template or sample. Run the reaction in the following PCR amplification conditions: 95 C for 5 min, then 95 C for 30 s, 52 C for 30 s, 72 C for 30 s for 20 cycles, followed by elongation at 40 C for 30 s. Keep PCR products at 4 C until ready to use.

For the real-time detection, a step 2 reaction is carried out using an identical procedure described in Example 3, where the 1 ul DNA template input is from the previous step 1, 20 cycle amplified product, and the primers are 1 µl of 10 uM forward primer (SEQ ID NO: 12, 5'-GCTCTTCGTGGT-GTGGTGTTTGTYGGATYGTGTGTATTT-3'; 1 µM final concentration) and 1 µl of 10 µM reverse primer (SEQ ID NO: 24, 5'-AACRTTCACRATAATCTCCATAC-3'; 1 µM final concentration).

Example 5: Detection of cccDNA in Liver Biopsies of Patients Infected With HBV

Liver tissue biopsies of HCC were acquired from patients infected with HBV and isolated DNA from these samples was subjected to bisulfite treatment. The bisulfite treated DNA was then tested by PCR for total HBV and tested by the 2-step BS-cccDNA assay (see FIG. 9).

Figure 9:
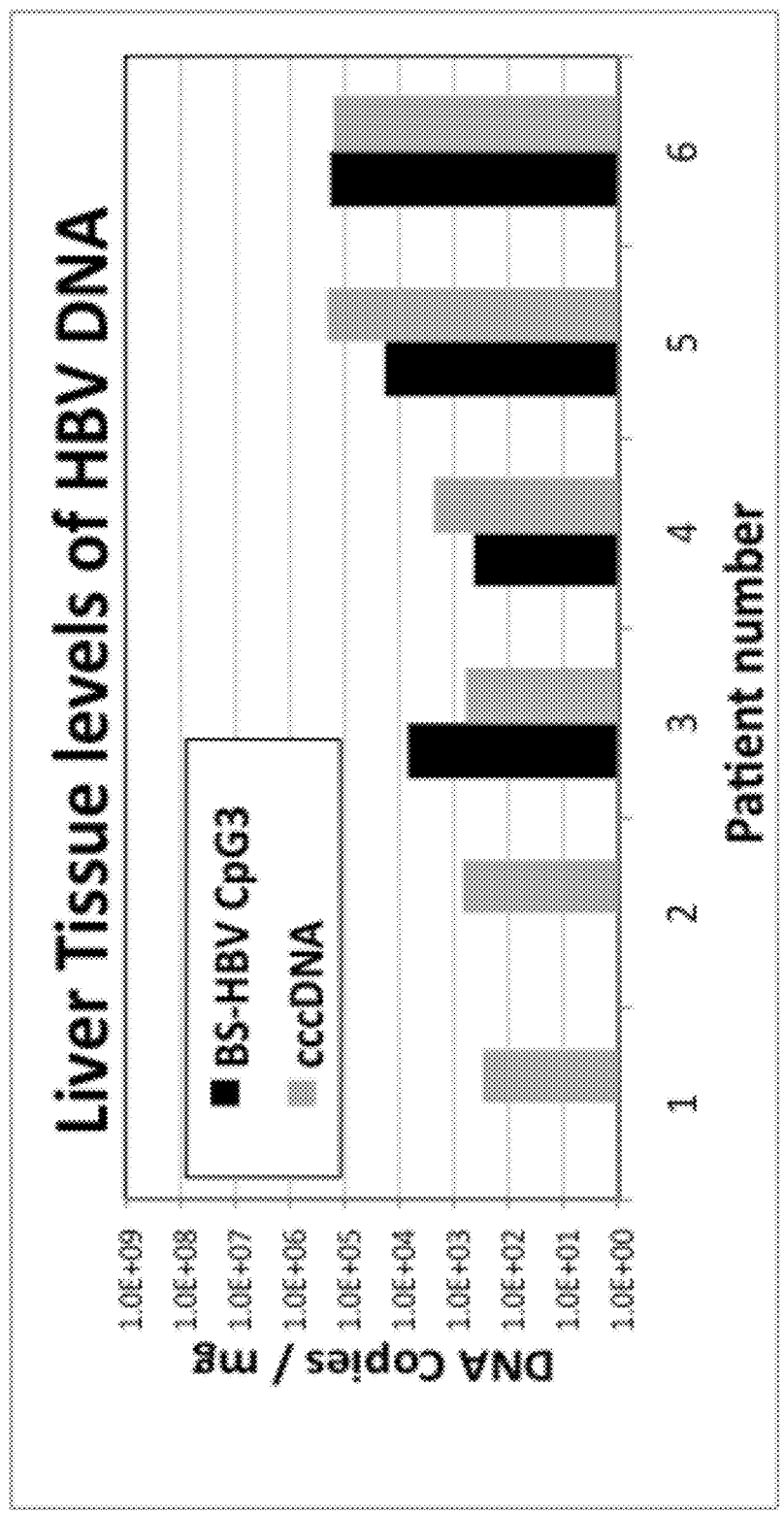
FIG. 9 depicts the amount of HBV DNA detected from tissue samples of patients infected with HBV.

FIG. 9 depicts the amount of HBV DNA detected from tissue samples of patients infected with HBV. The 2-step BS-cccDNA assay was used to detect cccDNA, and shows the amounts of cccDNA varied with HBV DNA in individuals. For patients 1 and 2, the HBV DNA levels were below the limit of detection for the HBV assay which is 100 copies per reaction, but the highly sensitive cccDNA assay was able to detect low levels of cccDNA.

Total HBV DNA input was less than $10^5$ copies, indicating that non-cccDNA (including rcDNA) should not detect by the two-step cccDNA assay. Therefore, amplification from this assay is clear evidence of specific cccDNA detection in HBV infected liver tissue samples.

REFERENCES

Abdelhamed, A. M., C. M. Kelley, T. G. Miller, P. A. Furman and H. C. Isom (2002). "Rebound of Hepatitis B Virus Replication in HepG2 Cells after Cessation of Antiviral Treatment". Journal of Virology 76(16): 8148-8160.

Ahmed, M., F. Wang, A. Levin, C. Le, Y. Eltayebi, M. Houghton, L. Tyrrell and K. Barakat (2015). "Targeting the Achilles heel of the hepatitis B virus: a review of current treatments against covalently closed circular DNA." Drug Discovery Today 20(5): 548-561.

Chen, Y., J. Sze and M.-L. He (2004). "HBV cccDNA in patients' sera as an indicator for HBV reactivation and an early signal of liver damage." World Journal of Gastroenterology 10(1): 82-85.

Guo, H., D. Jiang, T. Zhou, A. Cuconati, T. M. Block and J.-T. Guo (2007). "Characterization of the Intracellular Deproteinized Relaxed Circular DNA of Hepatitis B Virus: an Intermediate of Covalently Closed Circular DNA Formation". Journal of Virology 81(22): 12472-12484.

He, M. L., J. Wu, Y. Chen, M. C. Lin, G. K. K. Lau and H. f Kung (2002). "A new and sensitive method for the quantification of HBV cccDNA by real-time PCR". Biochemical and Biophysical Research Communications 295 (5): 1102-1107.

Kew M C (2010). "Epidemiology of chronic hepatitis B virus infection, hepatocellular carcinoma, and hepatitis B virus-induced hepatocellular carcinoma". Pathologie Biologie 58(4): 273-277.

Kumar, R., S. Pérez-del-Pulgar, B. Testoni, F. Lebossé and F. Zoulim (2016). "Clinical relevance of the study of hepatitis B virus covalently closed circular DNA". Liver International 36: 72-77.

Lavanchy, D. and M. Kane (2016). Global Epidemiology of Hepatitis B Virus Infection. Hepatitis B Virus in Human Diseases. Y.-F. Liaw and F. Zoulim. Cham, Springer International Publishing: 187-203.

Levrero, M., T. Pollicino, J. Petersen, L. Belloni, G. Raimondo and M. Dandri (2009). "Control of cccDNA function in hepatitis B virus infection". Journal of Hepatology 51(3): 581-592.

Li, W., J. Zhao, Z. Zou, Y. Liu, B. Li, Y. Sun, X. Li, S. Liu, S. Cai, W. Yao, S. Xin, F. Lu and D. Xu (2014). "Analysis of Hepatitis B Virus Intrahepatic Covalently Closed Circular DNA and Serum Viral Markers in Treatment-Naive Patients with Acute and Chronic HBV Infection". PLoS ONE 9(2): e89046.

Liu, F., M. Campagna, Y. Qi, X. Zhao, F. Guo, C. Xu, S. Li, W. Li, T. M. Block, J. Chang and J.-T. Guo (2013). "Alpha-Interferon Suppresses Hepadnavirus Transcription by Altering Epigenetic Modification of cccDNA Minichromosomes". PLoS Pathog 9(9): e1003613.

Nassal, M. (2015). "HBV cccDNA: viral persistence reservoir and key obstacle for a cure of chronic hepatitis B". Gut.

Petersen J, L. M., Volz T and Dandri M. (2007). "What is the Role of cccDNA in Chronic HBV Infection? Impact on HBV Therapy." Hepatology Reviews 9-13.

Shi, M., W.-L. Sun, Y.-Y. Hua, B. Han and L. Shi (2015). "Effects of Entecavir on Hepatitis B Virus Covalently Closed Circular DNA in Hepatitis B e Antigen-Positive Patients with Hepatitis B". PLoS ONE 10(2): e0117741.

Singh, M., A. Dicaire, A. E. Wakil, C. Luscombe and S. L. Sacks (2004). "Quantitation of hepatitis B virus (HBV) covalently closed circular DNA (cccDNA) in the liver of HBV-infected patients by LightCycler™ real-time PCR". Journal of Virological Methods 118(2): 159-167.

Takkenberg, R. B., H. L. Zaaijer, R. Molenkamp, S. Menting, V. Terpstra, C. J. Weegink, M. G. W. Dijkgraaf, P. L. M. Jansen, H. W. Reesink and M. G. H. M. Beld (2009). "Validation of a sensitive and specific real-time PCR for detection and quantitation of hepatitis B virus covalently closed circular DNA in plasma of chronic hepatitis B patients". Journal of Medical Virology 81(6): 988-995.

Tang, C.-M., T. O. Yau and J. Yu (2014). "Management of chronic hepatitis B infection: Current treatment guidelines, challenges, and new developments". World Journal of Gastroenterology: WJG 20(20): 6262-6278.

Tavis, J E, Gehring, A J, and Yuan Hu (2013). "How further suppression of virus replication could improve current HBV treatment". Expert Review of Anti-Infective Therapy 11(8): 755-757.

Wong, D. K.-H., M.-F. Yuen, H. Yuan, S. S.-M. Sum, C.-K. Hui, J. Hall and C.-L. Lai (2004). "Quantitation of covalently closed circular hepatitis B virus DNA in chronic hepatitis B patients". Hepatology 40(3): 727-737.

Wong, D. K., M. Yuen, H. J. Yuan, S. S. Sum, C. K. Hui, J. Hall and C. L. Lai (2004). "Quantitation of covalently closed circular hepatitis B virus DNA in chronic hepatitis B patients". Hepatology 40: 727-737.

Wu, Y., K. B. Johnson, G. Roccaro, J. Lopez, H. Zheng, A. Muiru, N. Ufere, R. Rajbhandari, O. Kattan and R. T. Chung (2014). "Poor Adherence to AASLD Guidelines for Chronic Hepatitis B Management and Treatment in a Large Academic Medical Center". Am J Gastroenterol 109(6): 867-875.

Zhong, Y., S. Hu, C. Xu, Y. Zhao, D. Xu, Y. Zhao, J. Zhao, Z. Li, X. Zhang, H. Zhang and J. Li (2014). "A novel method for detection of HBVcccDNA in hepatocytes using rolling circle amplification combined with in situ PCR". BMC Infectious Diseases 14: 608.

The invention claimed is:

1. A method for detecting or quantifying a closed covalent circular DNA (cccDNA) in a DNA sample containing the cccDNA and a non-cccDNA of a substantially same DNA sequence as, and of a different form from, the cccDNA, comprising:
   i) treating the DNA sample to abolish a complementary feature of, and to thereby prevent reannealing of two strands of, a double stranded DNA molecule in a treated DNA sample, whereby after said treating a treated cccDNA in the sample has two treated stands that are no longer complementary to each other; and
   ii) performing an amplification assay on the treated DNA sample such that the treated cccDNA, but not the non-cccDNA, can give rise to an amplified product.

2. The method of claim 1, wherein in step i) the DNA sample is treated by a chemical reagent, configured to alter sequences of, and to thereby abolish the complementary feature of, the two strands of the double stranded DNA molecule in the treated DNA sample.

3. The method of claim 2, wherein the chemical reagent acts by causing a deamination reaction.

4. The method of claim 3, wherein the deamination reaction is selective for a particular nucleotide.

5. The method of claim 1, wherein the amplification assay in step ii) is performed with a pair of primers, configured to respectively anneal to two strategic locations on the treated DNA sequence, and together configured to be able to generate an amplified product from the treated cccDNA, but not from the non-cccDNA.

6. The method of claim 5, wherein the two strategic locations are respectively on two sides of a known discontinuous region of a discontiguous strand in the non-cccDNA.

7. The method of claim 6, wherein the pair of primers are configured to respectively anneal to the two strategic locations of, and to thereby generate an amplified product from, a contiguous strand in the treated DNA sample.

8. The method of claim 7, wherein the amplification assay in step ii) comprises a real-time polymerase chain reaction (PCR), configured to quantify the cccDNA based on the amplified product.

9. The method of claim 7, wherein the amplification assay in step ii) is performed further with a probe, configured to anneal to the contiguous strand, but not to the discontiguous strand, in the treated DNA sample, and configured to allow a quantification of the cccDNA.

10. The method of claim 9, wherein the probe is labelled with a fluorescent dye and fluorescent quencher at a 5'-end and a 3'-end respectively, configured to allow a quantification of the cccDNA by measuring a fluorescent intensity.

11. The method of claim 1, wherein: the cccDNA comprises a cccDNA form of Hepatitis B virus (HBV); and the non-cccDNA comprises a relaxed circular DNA (rcDNA) form of HBV.

12. The method of claim 11, further comprising, prior to step i): obtaining the DNA sample from a biological sample, wherein the biological sample is a tissue or a body fluid.

13. The method of claim 12, wherein the body fluid is serum, plasma, blood, urine, or saliva.

14. A method of detecting in a sample cccDNA distinguishably from non-cccDNA, the method comprising (a) treating the sample with a nucleotide converter reagent whereby after said treating a treated cccDNA in the sample has two treated strands that are no longer complementary to each other; and (b) detecting the treated cccDNA by a PCR procedure.

15. The method of claim 14, wherein the nucleotide converter reagent is a deaminator.

16. The method of claim 14, wherein the PCR procedure uses a pair of primers that span a discontinuous region.

17. The method of claim 16, wherein the pair of primers are configured to respectively anneal to two strategic locations on two sides of the discontinuous region, and together configured to be able to generate an amplified product from the treated cccDNA, but not from the non-cccDNA.

18. The method of claim 16, wherein the PCR procedure further uses a probe, wherein the probe is configured to anneal to a contiguous strand, but not to a discontiguous strand.

* * * * *

SEQUENCE LISTING

```
<160> NUMBER OF SEQ ID NOS: 31

<210> SEQ ID NO 1
<211> LENGTH: 18
<212> TYPE: DNA
<213> ORGANISM: Artificial Sequence
<220> FEATURE:
<223> OTHER INFORMATION: Containing modified sequence from HBV DNA
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (11)..(11)
<223> OTHER INFORMATION: T/C

<400> SEQUENCE: 1
tttgtyggat ygtgtgta                                                 18

<210> SEQ ID NO 2
<211> LENGTH: 19
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (11)..(11)
<223> OTHER INFORMATION: T/C

<400> SEQUENCE: 2
tttgtyggat ygtgtgtat                                                19

<210> SEQ ID NO 3
<211> LENGTH: 20
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (11)..(11)
<223> OTHER INFORMATION: T/C

<400> SEQUENCE: 3
tttgtyggat ygtgtgtatt                                               20
```

```
<210> SEQ ID NO 4
<211> LENGTH: 21
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (11)..(11)
<223> OTHER INFORMATION: T/C

<400> SEQUENCE: 4
tttgtyggat ygtgtgtatt t                                              21

<210> SEQ ID NO 5
<211> LENGTH: 18
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: T/C
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (15)..(15)
<223> OTHER INFORMATION: T/C

<400> SEQUENCE: 5
ttaygyggtt ttttygtt                                                  18

<210> SEQ ID NO 6
<211> LENGTH: 19
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: T/C
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (15)..(15)
<223> OTHER INFORMATION: T/C

<400> SEQUENCE: 6
ttaygyggtt ttttygttt                                                 19

<210> SEQ ID NO 7
<211> LENGTH: 20
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: T/C
<220> FEATURE:
```

-continued

```
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (15)..(15)
<223> OTHER INFORMATION: T/C

<400> SEQUENCE: 7
ttaygyggtt ttttygtttg                                               20

<210> SEQ ID NO 8
<211> LENGTH: 21
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: T/C
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (15)..(15)
<223> OTHER INFORMATION: T/C

<400> SEQUENCE: 8
ttaygyggtt ttttygtttg t                                             21

<210> SEQ ID NO 9
<211> LENGTH: 18
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (5)..(5)
<223> OTHER INFORMATION: T/C
<220> FEATURE:
<221> NAME/KEY: misc_feature
<222> LOCATION: (9)..(9)
<223> OTHER INFORMATION: T/C
<220> FEATURE:
<221> NAME/KEY: misc_feature
<222> LOCATION: (15)..(15)
<223> OTHER INFORMATION: T/C

<400> SEQUENCE: 9
gtttyggtyg attayggg                                                 18

<210> SEQ ID NO 10
<211> LENGTH: 18
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (5)..(5)
<223> OTHER INFORMATION: T/C
<220> FEATURE:
<221> NAME/KEY: misc_feature
<222> LOCATION: (10)..(10)
<223> OTHER INFORMATION: T/C

<400> SEQUENCE: 10 attaygggy gtattttt                                                  18
```

<210> SEQ ID NO 11
<211> LENGTH: 55
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (40)..(40)
<223> OTHER INFORMATION: T/C
<220> FEATURE:
<221> NAME/KEY: misc_feature
<222> LOCATION: (45)..(45)
<223> OTHER INFORMATION: T/C

<400> SEQUENCE: 11
gtctcgtggg ctcggagatg tgtataagag acagtttgty ggatygtgtg tattt     55

<210> SEQ ID NO 12
<211> LENGTH: 39
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (24)..(24)
<223> OTHER INFORMATION: T/C
<220> FEATURE:
<221> NAME/KEY: misc_feature
<222> LOCATION: (29)..(29)
<223> OTHER INFORMATION: T/C

<400> SEQUENCE: 12
gctcttcgtg gtgtggtgtt tgtyggatyg tgtgtattt     39

<210> SEQ ID NO 13
<211> LENGTH: 38
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (22)..(22)
<223> OTHER INFORMATION: T/C
<220> FEATURE:
<221> NAME/KEY: misc_feature
<222> LOCATION: (24)..(24)
<223> OTHER INFORMATION: T/C
<220> FEATURE:
<221> NAME/KEY: misc_feature
<222> LOCATION: (33)..(33)
<223> OTHER INFORMATION: T/C

<400> SEQUENCE: 13
gctcttcgtg gtgtggtgtt aygyggttttt ttygtttg     38

<210> SEQ ID NO 14
<211> LENGTH: 25
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: T/C
<220> FEATURE:
<221> NAME/KEY: misc_feature
<222> LOCATION: (6)..(6)

```
<223> OTHER INFORMATION: T/C
<220> FEATURE:
<221> NAME/KEY: misc_feature
<222> LOCATION: (15)..(15)
<223> OTHER INFORMATION: T/C

<400> SEQUENCE: 14
ttaygyggtt ttttygtttg tgttt                                          25

<210> SEQ ID NO 15
<211> LENGTH: 24
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: T/C
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (15)..(15)
<223> OTHER INFORMATION: T/C

<400> SEQUENCE: 15
ttaygyggtt ttttygtttg tgtt                                           24

<210> SEQ ID NO 16
<211> LENGTH: 22
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: T/C
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (15)..(15)
<223> OTHER INFORMATION: T/C

<400> SEQUENCE: 16
ttaygyggtt ttttygtttg tg                                             22

<210> SEQ ID NO 17
<211> LENGTH: 21
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: T/C
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (15)..(15)
<223> OTHER INFORMATION: T/C

<400> SEQUENCE: 17
```
ttaygyggtt ttttygtttg t                                              21

<210> SEQ ID NO 18
<211> LENGTH: 43
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (22)..(22)
<223> OTHER INFORMATION: T/C
<220> FEATURE:
<221> NAME/KEY: misc_feature
<222> LOCATION: (24)..(24)
<223> OTHER INFORMATION: T/C
<220> FEATURE:
<221> NAME/KEY: misc_feature
<222> LOCATION: (33)..(33)
<223> OTHER INFORMATION: T/C

<400> SEQUENCE: 18
gctcttcgtg gtgtggtgtt aygyggtttt ttygtttgtg ttt                      43

<210> SEQ ID NO 19
<211> LENGTH: 42
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (22)..(22)
<223> OTHER INFORMATION: T/C
<220> FEATURE:
<221> NAME/KEY: misc_feature
<222> LOCATION: (24)..(24)
<223> OTHER INFORMATION: T/C
<220> FEATURE:
<221> NAME/KEY: misc_feature
<222> LOCATION: (33)..(33)
<223> OTHER INFORMATION: T/C

<400> SEQUENCE: 19
gctcttcgtg gtgtggtgtt aygyggtttt ttygtttgtg tt                       42

<210> SEQ ID NO 20
<211> LENGTH: 40
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (22)..(22)
<223> OTHER INFORMATION: T/C
<220> FEATURE:
<221> NAME/KEY: misc_feature
<222> LOCATION: (24)..(24)
<223> OTHER INFORMATION: T/C
<220> FEATURE:
<221> NAME/KEY: misc_feature
<222> LOCATION: (33)..(33)
<223> OTHER INFORMATION: T/C

<400> SEQUENCE: 20
gctcttcgtg gtgtggtgtt aygyggtttt ttygtttgtg                          40

<210> SEQ ID NO 21
<211> LENGTH: 39
<212> TYPE: DNA

```
<213> ORGANISM: Artificial Sequence
<220> FEATURE:
<223> OTHER INFORMATION: HBV
<220> FEATURE:
<221> NAME/KEY: misc_feature
<222> LOCATION: (22)..(22)
<223> OTHER INFORMATION: T/C
<220> FEATURE:
<221> NAME/KEY: misc_feature
<222> LOCATION: (24)..(24)
<223> OTHER INFORMATION: T/C
<220> FEATURE:
<221> NAME/KEY: misc_feature
<222> LOCATION: (33)..(33)
<223> OTHER INFORMATION: T/C

<400> SEQUENCE: 21
gctcttcgtg gtgtggtgtt aygyggtttt ttygtttgt                     39

<210> SEQ ID NO 22
<211> LENGTH: 25
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: G/A
<220> FEATURE:
<221> NAME/KEY: misc_feature
<222> LOCATION: (10)..(10)
<223> OTHER INFORMATION: G/A

<400> SEQUENCE: 22
aacrttcacr ataatctcca tacta                                    25

<210> SEQ ID NO 23
<211> LENGTH: 24
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: G/A
<220> FEATURE:
<221> NAME/KEY: misc_feature
<222> LOCATION: (10)..(10)
<223> OTHER INFORMATION: G/A

<400> SEQUENCE: 23
aacrttcacr ataatctcca tact                                     24

<210> SEQ ID NO 24
<211> LENGTH: 23
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: G/A
<220> FEATURE:
<221> NAME/KEY: misc_feature
<222> LOCATION: (10)..(10)
<223> OTHER INFORMATION: G/A

<400> SEQUENCE: 24
aacrttcacr ataatctcca tac                                      23
```

```
<210> SEQ ID NO 25
<211> LENGTH: 22
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: G/A
<220> FEATURE:
<221> NAME/KEY: misc_feature
<222> LOCATION: (10)..(10)
<223> OTHER INFORMATION: G/A

<400> SEQUENCE: 25
aacrttcacr ataatctcca ta                                              22

<210> SEQ ID NO 26
<211> LENGTH: 21
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: G/A
<220> FEATURE:
<221> NAME/KEY: misc_feature
<222> LOCATION: (10)..(10)
<223> OTHER INFORMATION: G/A

<400> SEQUENCE: 26
aacrttcacr ataatctcca t                                               21

<210> SEQ ID NO 27
<211> LENGTH: 20
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (4)..(4)
<223> OTHER INFORMATION: G/A
<220> FEATURE:
<221> NAME/KEY: misc_feature
<222> LOCATION: (10)..(10)
<223> OTHER INFORMATION: G/A

<400> SEQUENCE: 27
aacrttcacr ataatctcca                                                 20

<210> SEQ ID NO 28
<211> LENGTH: 41
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (22)..(22)
<223> OTHER INFORMATION: G/A
<220> FEATURE:
<221> NAME/KEY: misc_feature
<222> LOCATION: (28)..(28)
<223> OTHER INFORMATION: G/A

<400> SEQUENCE: 28
```
gctcttcgtg gtgtggtgaa crttcacrat aatctccata c                    41

<210> SEQ ID NO 29
<211> LENGTH: 35
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (1)..(1)
<223> OTHER INFORMATION: 6-FAM
<220> FEATURE:
<221> NAME/KEY: misc_feature
<222> LOCATION: (5)..(5)
<223> OTHER INFORMATION: T/C
<220> FEATURE:
<221> NAME/KEY: misc_feature
<222> LOCATION: (10)..(10)
<223> OTHER INFORMATION: T/C
<220> FEATURE:
<221> NAME/KEY: misc_feature
<222> LOCATION: (21)..(21)
<223> OTHER INFORMATION: T/C
<220> FEATURE:
<221> NAME/KEY: misc_feature
<222> LOCATION: (35)..(35)
<223> OTHER INFORMATION: BBQ

<400> SEQUENCE: 29
ttgtyggaty gtgtgtattt ygttttattt ttgta                    35

<210> SEQ ID NO 30
<211> LENGTH: 17
<212> TYPE: DNA
<213> ORGANISM: Artificial Sequence
<220> FEATURE:
<223> OTHER INFORMATION: HBV
<220> FEATURE:
<221> NAME/KEY: misc_feature
<222> LOCATION: (1)..(1)
<223> OTHER INFORMATION: 6FAM
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(14)
<223> OTHER INFORMATION: T/C
<220> FEATURE:
<221> NAME/KEY: misc_feature
<222> LOCATION: (15)..(15)
<223> OTHER INFORMATION: LNA
<220> FEATURE:
<221> NAME/KEY: misc_feature

```
<222> LOCATION: (16)..(16)
<223> OTHER INFORMATION: LNA
<220> FEATURE:
<221> NAME/KEY: misc_feature
<222> LOCATION: (17)..(17)
<223> OTHER INFORMATION: BBQ

<400> SEQUENCE: 30
ttttattttt gtaygta                                                    17

<210> SEQ ID NO 31
<211> LENGTH: 16
<212> TYPE: DNA
<213> ORGANISM: Artificial Sequence
<220> FEATURE:
<223> OTHER INFORMATION: Containing modified sequence from HBV DNA
<220> FEATURE:
<221> NAME/KEY: misc_feature
<222> LOCATION: (1)..(1)
<223> OTHER INFORMATION: 6FAM
<220> FEATURE:
<221> NAME/KEY: misc_feature
<222> LOCATION: (6)..(6)
<223> OTHER INFORMATION: T/C
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: T/C
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(14)
<223> OTHER INFORMATION: LNA
<220> FEATURE:
<221> NAME/KEY: misc_feature
<222> LOCATION: (16)..(16)
<223> OTHER INFORMATION: LNA
<220> FEATURE:
<221> NAME/KEY: misc_feature
<222> LOCATION: (16)..(16)
<223> OTHER INFORMATION: BBQ

<400> SEQUENCE: 31
tttgtyggat ygtgtg                                                     16
```